(12) United States Patent
Bolduc et al.

(10) Patent No.: US 8,883,848 B2
(45) Date of Patent: *Nov. 11, 2014

(54) ENHANCED MICROBIAL PERACID COMPOSITIONS AND METHODS OF USE AT REDUCED TEMPERATURES IN ASEPTIC CLEANING

(75) Inventors: John W. Bolduc, Eagan, MN (US); David D. McSherry, St. Paul, MN (US)

(73) Assignee: Ecolab USA Inc., Saint Paul, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 13/542,742

(22) Filed: Jul. 6, 2012

(65) Prior Publication Data

US 2013/0018097 A1 Jan. 17, 2013

Related U.S. Application Data

(60) Provisional application No. 61/507,678, filed on Jul. 14, 2011.

(51) Int. Cl.
| | | |
|---|---|---|
| A61K 31/19 | (2006.01) | |
| A01N 37/00 | (2006.01) | |
| A01N 59/00 | (2006.01) | |
| A01N 41/04 | (2006.01) | |
| A01N 37/16 | (2006.01) | |

(52) U.S. Cl.
CPC .......... *A01N 37/16* (2013.01); *A01N 59/00* (2013.01); *A01N 41/04* (2013.01)
USPC .......................................................... 514/557

(58) Field of Classification Search
CPC ....... A61K 31/19; A61K 31/20; A61K 8/365; A61K 31/195; A61Q 19/00
USPC ........................................................ 514/557
See application file for complete search history.

(56) References Cited

U.S. PATENT DOCUMENTS

| | | |
|---|---|---|
| 5,089,166 A | 2/1992 | Clements |
| 5,266,587 A | 11/1993 | Sankey et al. |
| 5,545,343 A | 8/1996 | Brougham et al. |
| 5,718,910 A | 2/1998 | Oakes et al. |
| 6,183,807 B1 | 2/2001 | Gutzmann et al. |
| 6,257,253 B1 * | 7/2001 | Lentsch et al. ............... 134/25.2 |
| 6,326,032 B1 | 12/2001 | Richter et al. |
| 6,384,006 B1 | 5/2002 | Wei et al. |
| 6,544,942 B1 | 4/2003 | Smith et al. |
| 6,593,283 B2 | 7/2003 | Hei et al. |
| 6,627,657 B1 | 9/2003 | Hilgren et al. |
| 6,927,237 B2 | 8/2005 | Hei et al. |
| 6,964,788 B2 | 11/2005 | Phebus et al. |
| 6,998,369 B2 | 2/2006 | Hei et al. |
| 7,060,301 B2 | 6/2006 | Wei et al. |
| 7,498,051 B2 * | 3/2009 | Man et al. ..................... 426/332 |
| 7,622,606 B2 | 11/2009 | Smith et al. |
| 7,767,769 B2 | 8/2010 | Glos |
| 7,816,555 B2 | 10/2010 | Smith et al. |
| 8,124,132 B2 | 2/2012 | Hilgren et al. |
| 2001/0001786 A1 | 5/2001 | Scialla et al. |
| 2002/0128312 A1* | 9/2002 | Hei et al. ....................... 514/529 |
| 2003/0026846 A1 | 2/2003 | Hei et al. |
| 2003/0234382 A1 | 12/2003 | Sato et al. |
| 2003/0235623 A1 | 12/2003 | Van Oosterom |
| 2004/0033269 A1 | 2/2004 | Hei et al. |
| 2005/0288204 A1 | 12/2005 | Matts et al. |
| 2006/0228323 A1 | 10/2006 | Novelle et al. |
| 2009/0104073 A1 | 4/2009 | Kaiser et al. |
| 2009/0104172 A1 | 4/2009 | Christensen et al. |
| 2009/0208365 A1 | 8/2009 | McSherry et al. |
| 2009/0263539 A1 | 10/2009 | Herdt et al. |
| 2009/0269324 A1 | 10/2009 | Herdt et al. |
| 2010/0021557 A1 | 1/2010 | Li et al. |
| 2010/0048730 A1 | 2/2010 | Li et al. |
| 2010/0086621 A1 | 4/2010 | DiCosimo et al. |
| 2010/0227000 A1 | 9/2010 | Ames et al. |
| 2011/0294408 A1 | 12/2011 | Hilgren et al. |

FOREIGN PATENT DOCUMENTS

| | | |
|---|---|---|
| DE | 101 21 809 A1 | 11/2002 |
| JP | 2008-222688 A | 9/2008 |
| WO | WO 00/22931 A1 | 4/2000 |
| WO | WO02088076 A2 | 11/2002 |
| WO | WO 2011/005270 A1 | 1/2011 |
| WO | WO 2011/027892 A1 | 3/2011 |
| WO | WO 2011/079080 A1 | 6/2011 |
| WO | WO 2011/138682 A2 | 11/2011 |
| WO | WO 2011/138682 A3 | 11/2011 |
| WO | WO 2011/146557 A1 | 11/2011 |
| WO | WO 2012/010198 A1 | 1/2012 |
| WO | WO 2012/045364 A2 | 4/2012 |

OTHER PUBLICATIONS

Jim Clark (2004) 1-4 pages (http://www.chemguide.co.uk/organicprops/acids/esterification.html).*
Ecolab USA Inc. et al., PCT/US2012/046076, "Notification of Transmittal of the International Search Report and The Written Opinion of the International Searching Authority, or The Declaration", mail date Jan. 30, 2013.
Ecolab USA Inc. et al., PCT/US2012/046059, "Notification of Transmittal of the International Search Report and The Written Opinion of the International Searching Authority, or The Declaration", mail date Jan. 30, 2013.
DE 101 21 809 A1, Widulle, Herbert, English Abstract, 1 page, (Jul. 11, 2002).
JP 2008-222688 A, Mitsubishi Gas Chemical Co., English Abstract, 1 page, (2008).

* cited by examiner

*Primary Examiner* — Shirley V Gembeh
(74) *Attorney, Agent, or Firm* — McKee, Voorhees & Sease

(57) ABSTRACT

The present invention relates to compositions of peracids, such as peroxycarboxylic acids, having improved antimicrobial efficacy due to ethanol solubilization of the compositions. The enhanced antimicrobial efficacy of the peracid compositions beneficially have a lower use concentration. The invention further relates to methods employing such compositions.

19 Claims, 2 Drawing Sheets

US 8,883,848 B2

ENHANCED MICROBIAL PERACID COMPOSITIONS AND METHODS OF USE AT REDUCED TEMPERATURES IN ASEPTIC CLEANING

CROSS-REFERENCE TO RELATED APPLICATIONS

This application claims priority to U.S. Provisional Application Ser. No. 61/507,678 filed on Jul. 14, 2011 and entitled Deodorization of Peracids. The entire contents of this patent application are hereby expressly incorporated herein by reference including, without limitation, the specification, claims, and abstract, as well as any figures, tables, or drawings thereof.

This application is also related to U.S. application Ser. No. 13/542,735 filed simultaneously herewith and entitled Deodorization of Peracids. The entire contents of this patent application are also expressly incorporated herein by reference including, without limitation, the specification, claims, and abstract, as well as any figures, tables, or drawings thereof.

FIELD OF THE INVENTION

The invention relates to compositions of peracids, such as mixed peroxycarboxylic acid compositions, having improved antimicrobial efficacy compared to conventional peracid compositions due in part to the solubilization of the mixed peracid compositions using esters. The present invention further relates to methods employing the enhanced microbial efficacy compositions at reduced temperatures, including for example, use in aseptic cleaning. In a particular aspect of the invention, the improved antimicrobial peracid compositions include an alcohol or esters for the solubilization of the peracids to generate compositions having a lower use concentration.

BACKGROUND OF THE INVENTION

Peracid compositions, namely peroxycarboxylic acid compositions, exhibit useful antimicrobial and bleaching activity. Conventional peroxycarboxylic acid compositions typically include short chain peroxycarboxylic acids or mixtures of short chain peroxycarboxylic acids and medium chain peroxycarboxylic acids (see, e.g., U.S. Pat. Nos. 5,200,189, 5,314,687, 5,409,713, 5,437,868, 5,489,434, 6,674,538, 6,010,729, 6,111,963, and 6,514,556, each incorporated by reference in its entirety). However, peracid compositions have a number of limitations, including malodors, stability concerns and insufficient micro efficacy against certain microorganisms.

A majority of existing peracid compositions, including peroxycarboxylic acids, suffer from unacceptable odors which are an inherent disadvantage of the compositions and limit their use in cleaning applications. Often the peracid compositions exhibit a sharp, annoying, or otherwise unacceptable odor that increases as the composition ages, beginning within as soon as a few weeks of formulation. Such malodors significantly limit the applications suitable for using such peroxycarboxylic acid compositions. It would be undesirable to apply such peroxycarboxylic acid compositions to large surfaces areas (e.g. floor cleaners).

There is a need for antimicrobial agents having improved antimicrobial efficacy. Although many peracid compositions have a broad spectrum of antimicrobial properties, many have inadequate activity against hard to kill pathogens, including bacterial spores, fungal spores, and fungi. As a result, killing, inactivating, or otherwise reducing the active population of bacterial spores and fungi on surfaces is particularly difficult. The bacterial spore-forming microorganisms of the *Bacillus* species are especially important to be aware of during food packaging, particularly during cold or hot aseptic filling of food and beverage, or pharmaceutical, products. Microorganisms of the *Bacillus* species include *Bacillus atropheaus, Bacillus cereus, Bacillus mycoides, Bacillus subtilis, Bacillus anthracis*, and *Bacillus thuringiensis*. These latter microorganisms share many phenotypical properties, have a high level of chromosomal sequence similarity, and are known enterotoxin producers. *Bacillus cereus* is one of the most problematic because *Bacillus cereus* has been identified as possessing increased resistance to germicidal chemicals used to decontaminate environmental surfaces. For example, Blakistone et al., Efficacy of Oxonia Active Against Selected Sporeformers, Journal of Food Protection, Volume 62, pages 262 267, report that *Bacillus cereus* was more tolerant to the effects of conventionally formulated peroxyacetic acid germicides than all other spore-forming bacteria tested, including other *Bacillus* and *Clostridium* species.

According to the invention, there is a need for improved stability antimicrobial peroxycarboxylic acid compositions.

It is an objective of the claimed invention to develop improved peracid chemistry for use at lower use concentrations and temperatures.

A further object of the invention is an improved peracid composition with enhanced microbial efficacy for targeting endospore-forming bacilli type bacteria.

A further object of the invention is a method of use for applications employing a lower use concentration of a peracid composition having enhanced microbial efficacy.

A further object of the invention is to provide improved peracid compositions and methods for using the compositions for clean in place (CIP) applications, for example cleaning of tanks, lines, pumps and other process equipment used for processing typically liquid product streams of beverages, in particular for cleaning milking machines.

A still further object of the invention is to provide improved peracid compositions and methods for using the compositions for clean out of place (COP) applications, for example cleaning the interior and exterior surfaces of a wide variety of parts, such as ceramic surfaces, metal surfaces, walls in, wash tanks, soaking vessels, mop buckets, holding tanks, scrub sinks, vehicle parts washers, non-continuous batch washers and systems, and the like.

BRIEF SUMMARY OF THE INVENTION

The present invention relates to peracid compositions having improved antimicrobial efficacy compared to conventional peracid compositions, and methods employing these improved peracid compositions. Typically, the compositions according to the present invention include an alcohol for esterification of peracids to eliminate the shorter chain carboxylic acids responsible for malodor along with providing improved solubilization of the peracid compositions. Alternatively, esters can be added directly to a preformed peracid composition according to the invention in order to provide the same benefits, such as improved antimicrobial efficacy along with use of the peracid compositions at lower use concentrations and temperatures.

In an aspect of the invention, an enhanced peroxycarboxylic acid composition for use at reduced concentrations and temperatures is provided and comprises at least one $C_1$-$C_{22}$ carboxylic acid; at least one $C_1$-$C_{22}$ percarboxylic acid;

hydrogen peroxide; a surfactant or an sulfonated carboxylic acid and a corresponding sulfonated percarboxylic acid; and an alcohol, wherein the concentration of the peroxycarboxylic acids is less than about 2000 ppm and is effective against *Bacillus* species at temperatures at or below about 50° C.

In an aspect of the invention, an enhanced peroxycarboxylic acid composition for use at reduced concentrations and temperatures is provided and comprises at least one C1-C22 carboxylic acid selected from the group consisting of acetic acid, octanoic acid, sulfonated oleic acid and combinations thereof; at least one C1-C22 percarboxylic acid selected from the group consisting of peracetic acid, peroctanoic acid, persulfonated oleic acid and combinations thereof; hydrogen peroxide; and an alcohol, wherein the composition is slightly water insoluble at a use solution, wherein the composition provides a concentration less than about 2000 ppm of said C1-C22 percarboxylic acid, wherein the composition is effective against *Bacillus* species at temperatures at or below about 50° C., and wherein the alcohol generates ester species providing a pleasant odor masking and/or derivatizing the malodors associated with the percarboxylic acids and carboxylic acids.

In a still further aspect of the invention, a method of reducing population of microorganism on an object at reduced temperatures and concentrations is provided. The methods may include the steps of: providing a mixed peroxycarboxylic acid composition comprising at least one peroxycarboxylic acid, at least one sulfoperoxycarboxylic acid, and either an ester or an alcohol (e.g. short chain alcohol) for forming an ester in the mixed peroxycarboxylic acid composition, wherein the concentration of active peroxycarboxylic acid and sulfoperoxycarboxylic acid is less than about 2000 ppm; and contacting an object with the mixed peroxycarboxylic acid composition at a temperature below about 50° C.

While multiple embodiments are disclosed, still other embodiments of the present invention will become apparent to those skilled in the art from the following detailed description, which shows and describes illustrative embodiments of the invention.

Accordingly, the drawings and detailed description are to be regarded as illustrative in nature and not restrictive.

Figure 1:
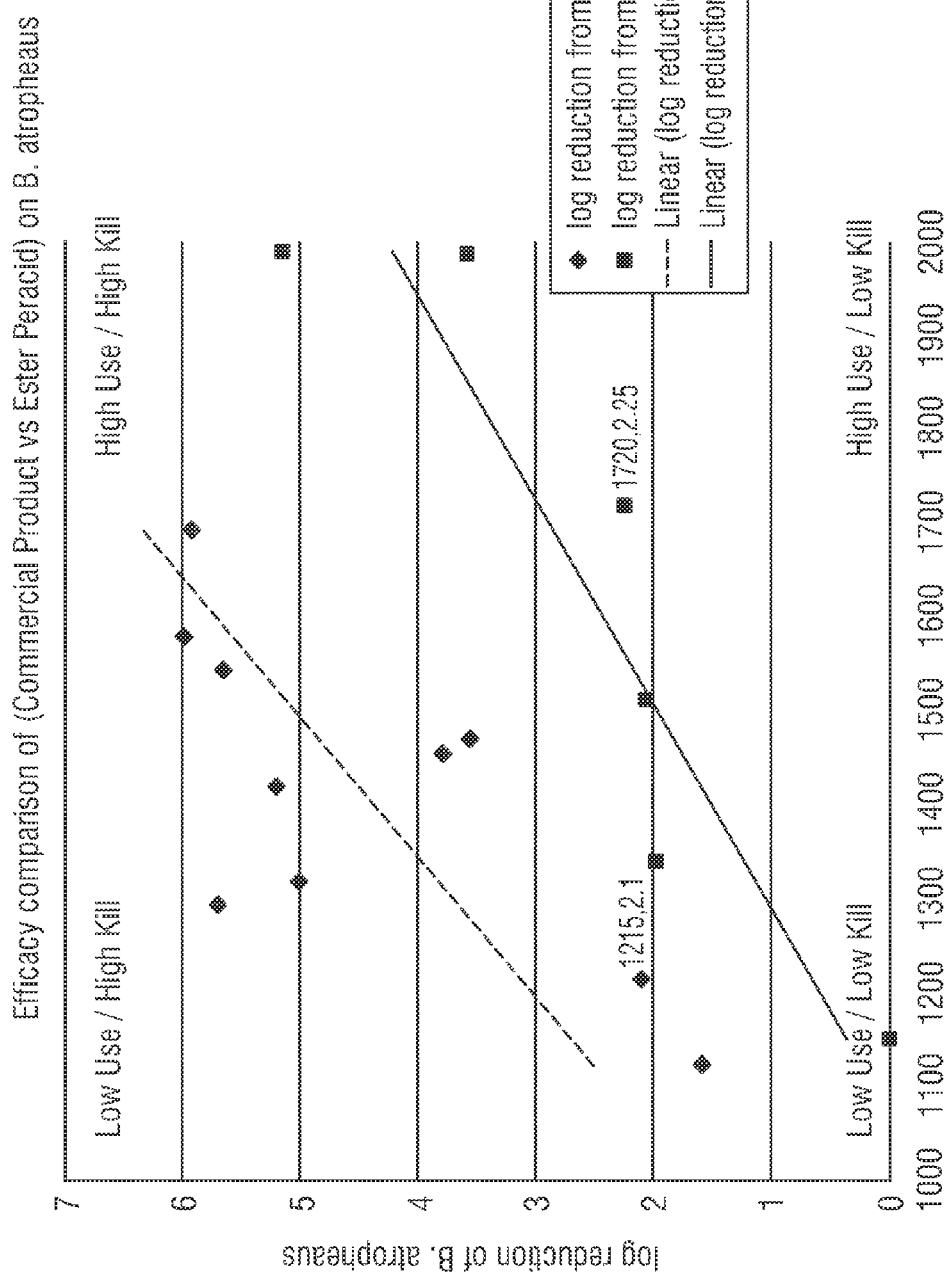
FIGS. 1-2 show graphs comparing the micro efficacy of mixed ester peracid compositions according to the invention in comparison to a single peracid composition, demonstrating a benefit of the invention in reducing concentration of peracid compositions along with reducing use temperatures while providing at least 5 log-order reduction in microorganisms.

Various embodiments of the present invention will be described in detail with reference to the drawings, wherein like reference numerals represent like parts throughout the several views. Reference to various embodiments does not limit the scope of the invention. Figures represented herein are not limitations to the various embodiments according to the invention and are presented for exemplary illustration of the invention.

DETAILED DESCRIPTION OF THE PREFERRED EMBODIMENT

The present invention relates to enhanced antimicrobial peracid compositions including an effective antimicrobial amount of a peracid and an alcohol for esterification of the peracid compositions to form alkyl esters. Alternatively, esters can be added directly to a preformed peracid composition according to the invention. Beneficially, the compositions of the invention have improved antimicrobial efficacy, requiring lower use concentrations, compared to a conventional peracid composition lacking the alcohol. As a result, the present antimicrobial peracid composition can be used at a lower use concentration while effectively reducing microbial populations, including difficult to kill endospore forming bacilli type bacteria which are not killed by commodity peracid compositions. As a result, the compositions can be used on a variety of hard surfaces such as those in facilities and equipment used in the food and beverage industries. Additionally, the present composition can be used to effectively reduce the microbial population of food, of dishware, and to treat water. In a still further benefit of the invention, the use of esters in the peracid compositions according to the invention results in an improved odor profile for the peracid composition.

The embodiments of this invention are not limited to particular compositions, methods of use and methods of making, which can vary and are understood by skilled artisans. It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form. Numeric ranges recited within the specification are inclusive of the numbers defining the range and include each integer within the defined range.

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The term "about," as used herein, refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities refers to variation in the numerical quantity that can occur.

The term "alkyl" or "alkyl groups," as used herein, refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups). Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can affect two kinds of microbial cell damage. The first is a lethal, irreversible action resulting in complete microbial cell destruction or incapacitation. The second type of cell damage is reversible, such that if the organism is rendered free of the agent, it can again multiply. The former is termed bacteriocidal and the later, bacteriostatic. A sanitizer and a disinfectant are, by definition, agents which provide antibacterial or bacteriocidal activity. In contrast, a preservative is generally described as an inhibitor or bacteriostatic composition.

For the purpose of this patent application, successful reduction of microorganisms is achieved when the populations of microorganisms are reduced by about 50%, by significantly more than is achieved by a wash with water, or at least about 0.3-1 $\log_{10}$: Larger reductions in microbial population provide greater levels of protection. In this application, such a population reduction is the minimum acceptable for the processes. Any increased reduction in population of microorganisms is an added benefit that provides higher levels of protection.

The term "disinfectant," as used herein, refers to an agent that kills all vegetative cells including most recognized pathogenic microorganisms, using the procedure described in A.O.A.C. Use Dilution Methods, Official Methods of Analysis of the Association of Official Analytical Chemists, paragraph 955.14 and applicable sections, 15$^{th}$ Edition, 1990 (EPA Guideline 91-2). As used herein, the term "high level disinfection" or "high level disinfectant" refers to a compound or composition that kills substantially all organisms, except high levels of bacterial spores, and is effected with a chemical germicide cleared for marketing as a sterilant by the Food and Drug Administration. As used herein, the term "intermediate-level disinfection" or "intermediate level disinfectant" refers to a compound or composition that kills mycobacteria, most viruses, and bacteria with a chemical germicide registered as a tuberculocide by the Environmental Protection Agency (EPA). As used herein, the term "low-level disinfection" or "low level disinfectant" refers to a compound or composition that kills some viruses and bacteria with a chemical germicide registered as a hospital disinfectant by the EPA.

The phrase "food processing surface" or, "food surface," as used herein, refers to a surface of a tool, a machine, equipment, a structure, a building, or the like that is employed as part of a food processing, preparation, or storage activity. Examples of food processing surfaces include surfaces of food processing or preparation equipment (e.g., slicing, canning, or transport equipment, including flumes), of food processing wares (e.g., utensils, dishware, wash ware, and bar glasses), and of floors, walls, or fixtures of structures in which food processing occurs. Food processing surfaces are found and employed in food anti-spoilage air circulation systems, aseptic packaging sanitizing, food refrigeration and cooler cleaners and sanitizers, ware washing sanitizing, blancher cleaning and sanitizing, food packaging materials, cutting board additives, third-sink sanitizing, beverage chillers and warmers, meat chilling or scalding waters, sanitizing gels, cooling towers, food processing antimicrobial garment sprays, and non-to-low-aqueous food preparation lubricants, oils, and rinse additives.

The phrase "health care surface," as used herein, refers to a surface of an instrument, a device, a cart, a cage, furniture, a structure, a building, or the like that is employed as part of a health care activity. Examples of health care surfaces include surfaces of medical or dental instruments, of medical or dental devices, of electronic apparatus employed for monitoring patient health, and of floors, walls, or fixtures of structures in which health care occurs. Health care surfaces are found in hospital, surgical, infirmary, birthing, mortuary, and clinical diagnosis rooms. These surfaces can be those typified as "hard surfaces" (such as walls, floors, bed-pans, etc.,), or woven and non-woven surfaces (such as surgical garments, draperies, bed linens, bandages, etc.), or patient-care equipment (such as respirators, diagnostic equipment, shunts, body scopes, wheel chairs, beds, etc.), or surgical and diagnostic equipment. Health care surfaces include articles and surfaces employed in animal health care.

The term "heterocyclic group," as used herein (e.g. referring to substituted alkyls including a heterocyclic group), includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

The term "instrument," as used herein, refers to the various medical or dental instruments or devices that can benefit from cleaning with a reduced-odor composition according to the present invention. The phrases "medical instrument", "dental instrument", "medical device", "dental device", "medical equipment", or "dental equipment" refer to instruments, devices, tools, appliances, apparatus, and equipment used in medicine or dentistry. Such instruments, devices, and equipment can be cold sterilized, soaked or washed and then heat sterilized, or otherwise benefit from cleaning in a composition of the present invention. These various instruments, devices and equipment include, but are not limited to: diagnostic instruments, trays, pans, holders, racks, forceps, scissors, shears, saws (e.g. bone saws and their blades), hemostats, knives, chisels, rongeurs, files, nippers, drills, drill bits, rasps, burrs, spreaders, breakers, elevators, clamps, needle holders, carriers, clips, hooks, gouges, curettes, retractors, straightener, punches, extractors, scoops, keratomes, spatulas, expressors, trocars, dilators, cages, glassware, tubing, catheters, cannulas, plugs, stents, arthoscopes and related equipment, and the like, or combinations thereof.

The terms "agricultural" or "veterinary" objects or surfaces, as used herein, include animal feeds, animal watering stations and enclosures, animal quarters, animal veterinarian clinics (e.g. surgical or treatment areas), animal surgical areas, and the like.

The term "microorganisms," as used herein, refers to any noncellular or unicellular (including colonial) organism. Microorganisms include all prokaryotes. Microorganisms include bacteria (including cyanobacteria), lichens, microfungi, protozoa, virinos, viroids, viruses, and some algae. As used herein, the term "microbe" is synonymous with microorganism.

The terms "mixed" or "mixture" when used relating to "peracid composition," "peroxycarboxylic acid composition," "peracids" or "peroxycarboxylic acids" refer to a composition or mixture including more than one peracid, such as a peroxycarboxylic acid, such as a composition or mixture including peroxyacetic acid and peroxyoctanoic acid.

The phrases "objectionable odor," "offensive odor," or "malodor," as used herein, refer to a sharp, pungent, or acrid odor or atmospheric environment from which a typical person withdraws if they are able to. Hedonic tone provides a measure of the degree to which an odor is pleasant or unpleasant. An "objectionable odor," "offensive odor," or "malodor" has an hedonic tone rating it as unpleasant as or more unpleasant than a solution of 5 wt-% acetic acid, propionic acid, butyric acid, or mixtures thereof.

The term "object", as used herein, refers to a something material that can be perceived by the senses, directly and/or indirectly. Objects include a surface, including a hard surface (such as glass, ceramics, metal, natural and synthetic rock, wood, and polymeric), an elastomer or plastic, woven and non-woven substrates, a food processing surface, a health care surface, and the like. Objects also include a food product (and its surfaces); a body or stream of water or a gas (e.g., an air stream); and surfaces and articles employed in hospitality and industrial sectors.

The term "sanitizer," as used herein, refers to an agent that reduces the number of bacterial contaminants to safe levels as judged by public health requirements. In an embodiment, sanitizers for use in this invention will provide at least a 99.999% reduction (5-log order reduction). These reductions can be evaluated using a procedure set out in Germicidal and Detergent Sanitizing Action of Disinfectants, Official Methods of Analysis of the Association of Official Analytical Chemists, paragraph 960.09 and applicable sections, 15$^{th}$ Edition, 1990 (EPA Guideline 91-2). According to this reference a sanitizer should provide a 99.999% reduction (5-log order reduction) within 30 seconds at room temperature, 25° C.+/−2° C., against several test organisms.

The phrase "short chain carboxylic acid," as used herein, refers to a carboxylic acid that has characteristic bad, pungent, or acrid odor. Examples of short chain carboxylic acids include formic acid, acetic acid, propionic acid, and butyric acid.

The term "sporicide," as used herein, refers to a physical or chemical agent or process having the ability to cause greater than a 90% reduction (1-log order reduction) in the population of spores, such as spores of Bacillus cereus, Bacillus atropheaus or Bacillus subtilis, within 30 minutes at ambient temperature. In certain embodiments, the sporicidal compositions of the invention provide greater than a 99% reduction (2-log order reduction), greater than a 99.99% reduction (4-log order reduction), or greater than a 99.999% reduction (5-log order reduction) in such population within at least 30 minutes at ambient temperature. In preferred aspects, the sporicidal reduction in such populations is preferably effective within 10 seconds at 60° C.

The term "ware," as used herein, refers to items such as eating and cooking utensils, dishes, and other hard surfaces such as showers, sinks, toilets, bathtubs, countertops, windows, mirrors, transportation vehicles, and floors. As used herein, the term "warewashing" refers to washing, cleaning, or rinsing ware. Ware also refers to items made of plastic. Types of plastics that can be cleaned with the compositions according to the invention include but are not limited to, those that include polycarbonate polymers (PC), acrilonitrile-butadiene-styrene polymers (ABS), and polysulfone polymers (PS). Another exemplary plastic that can be cleaned using the compounds and compositions of the invention include polyethylene terephthalate (PET).

As used herein, the term "water soluble" refers to a compound that can be dissolved in water at a concentration of more than 1 wt-%. The terms "slightly soluble" or "slightly water soluble" refer to a compound that can be dissolved in water only to a concentration of 0.1 to 1.0 wt-%. In addition, the term "water insoluble" refers to a compound that can be dissolved in water only to a concentration of less than 0.1 wt-%.

The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

The methods and compositions of the present invention may comprise, consist essentially of, or consist of the component and ingredients of the present invention as well as other ingredients described herein. As used herein, "consisting essentially of" means that the methods and compositions may include additional steps, components or ingredients, but only if the additional steps, components or ingredients do not materially alter the basic and novel characteristics of the claimed methods and compositions.

Peracid Compositions

While an understanding of the mechanism is not necessary to practice the present invention and while the present invention is not limited to any particular mechanism of action, it is contemplated that, in some embodiments, the peroxycarboxylic acid compositions using an alcohol, such as ethanol, can remove and/or mask short chain malodors inherent in traditional peracids as well as provide solubilization and/or efficacy benefits for the resultant peroxycarboxylic acid composition. In an further aspect of the invention, the use of esters (as opposed to causing esterification reactions by employing an alcohol) in peroxycarboxylic acid compositions can provide the same benefits.

As one skilled in the art appreciates, peracid compositions change with age. The malodors commonly associated with peroxycarboxylic acid compositions are indicative of the degradation of peroxycarboxylic acids over time. Certain benefits of employing the peroxycarboxylic acid compositions according to the invention and the methods of the invention involve the reduction, masking and/or eliminating of odors as a result of employing alcohols and/or esters. For example, without being limited to a particular theory, use of an alcohol in a (or an ester provided directly to a preformed) peroxycarboxylic acid composition forms water soluble esters. Further description of these benefits and compositions and/or methods for employing the same are disclosed in to U.S. application Ser. No. 13/542,735 filed simultaneously herewith, which is incorporated herein by reference in its entirety.

According to an embodiment of the invention, and not intending to be limited to a particular theory, the use of an ester in the peroxycarboxylic acid compositions provides water soluble esters. The addition of a water soluble or marginally water soluble ester to the peroxycarboxylic acid compositions results in numerous benefits, including for example, enhanced micro efficacy of the peroxycarboxylic acids. In particular, according to a preferred embodiment of the invention, the enhanced micro efficacy of the peroxycarboxylic acids provides antimicrobial activity against resistant endospore forming pathogens, including for example, *Bacillus* and *Clostridium*, including *B. cereus, B. subtilus, B. atropheaus* and *C. difficile*.

The present invention relates to enhanced antimicrobial compositions containing peroxycarboxylic acids and esters. In a further aspect, the present invention relates to enhanced antimicrobial compositions containing peroxycarboxylic acids and an alcohol for an esterification reaction to form esters in the resultant peroxycarboxylic acids.

In certain embodiments of the invention, the enhanced antimicrobial compositions further include an acidic anionic surfactant and/or hydrotrope surfactant. Beneficially, the peroxycarboxylic acids and the acidic anionic surfactant, which may be a persulfonated oleic acid, are both antimicrobial agents. In other aspects, the compositions do not employ any surfactants, such as hydrotrope surfactants, or employ minimal amounts of the surfactants.

In certain preferred aspects of the invention, mixed peroxycarboxylic acids (such as an equilibrium composition of mixed peroxycarboxylic acids) are combined with the acidic anionic surfactant persulfonated oleic acid in amounts as low as about 1 wt-%, or as low as 0.1 wt 0%, or as low as 0.01 wt-%, or still further as low as 0.001 wt-%. Beneficially, the minimal amount of persulfonated oleic acid provides both the benefits of an anionic surfactant (e.g. foaming profile and removing peroxycarboxylic acids during various cleaning and/or sanitizing processes) as well as the additional micro efficacy achieved from the formulation of a mixed peracid composition.

Surprisingly the peroxycarboxylic acid compositions according to the invention do not exhibit the unacceptable odor commonly associated with mixed and/or single peracid compositions.

Exemplary compositions according to the invention are provided as follows for both pre-equilibrium and post-equilibrium compositions:

| | %, w/w | %, w/w | %, w/w |
|---|---|---|---|
| Pre-equilibrium | | | |
| Alcohol | 0.1-20% | 0.1-10% | 1-10% |
| Carboxylic acid(s) (C1-C22) | 0.1-80% | 0.1-50% | 1-50% |
| Oxidizing Agent | 0.1-80% | 1-80% | 10-75% |
| Optional Stabilizing Agent(s) | 0.01-20% | 0.1-10% | 0.1-5% |
| Optional Surfactant(s) | 0.001-20% | 0.01-10% | 0.01-5% |
| | 100.00% | 100.00% | 100.00% |
| Post-equilibrium | | | |
| Esters | 0.01-20% | 0.1-20% | 1-20% |
| Carboxylic acid(s) (C1-C22) | 0.1-80% | 0.1-40% | 1-40% |
| Peroxycarboxylic Acid(s) (C1-C22) | 0.01-50% | 0.1-50% | 1-50% |
| Oxidizing Agent | 0.1-80% | 1-80% | 1-40% |
| Optional Stabilizing Agent(s) | 0.001-10% | 0.01-10% | 0.01-2% |
| Optional Surfactant(s) | 0.0001-10% | 0.001-10% | 0.01-1% |
| Water | 1-60% | 5-60% | 10-50% |
| | 100.00% | 100.00% | 100.00% |

Suitable levels of an alcohol or ester in a concentrate composition according to the invention include a mole ratio of alcohol or ester to peroxycarboxylic acid of at least from about 160:1 alcohol or ester to peracid to about 1:10 for a concentrate composition according to the invention. In a preferred embodiment, the mole ratio of alcohol or ester to peroxycarboxylic acid for a concentrate composition is from about 120:1 to about 1:20, or from about 100:1 to about 1:25. It is to be understood that all ranges and values between these ranges and values are encompassed by the present invention.

In an embodiment of the invention, a concentrate pre-equilibrium composition may include from about 1 to 80 wt-% carboxylic acids and from about 0.1 to 20 wt-% alcohol. It is to be understood that all ranges and values between these ranges and values are encompassed by the present invention.

Suitable levels of an alcohol in a ready to use (RTU) composition according to the invention include a mole ratio of peroxycarboxylic acid to alcohol or ester of at least from about 500:1 to about 3:1. In a preferred embodiment, the mole ratio of peroxycarboxylic acid to alcohol or ester for a RTU composition is from about 500:1 to about 10:1, or from about 1400:1 to about 20:1. It is to be understood that all ranges and values between these ranges and values are encompassed by the present invention.

In an embodiment of the invention, a RTU pre-equilibrium composition includes about 0.1 to 50 wt-% carboxylic acids and from about 0.01 wt-% to 10 wt-% alcohol. RTU compositions may be further diluted according to embodiments of the invention disclosed herein. It is to be understood that all ranges and values between these ranges and values are encompassed by the present invention.

Beneficially, the use solutions of the post-equilibrium mixed peroxycarboxylic acid compositions of the invention have lower use concentrations that conventional single species peracid compositions, including single species peracid compositions customarily employed in aseptic cleaning and/or filling applications. In an embodiment of the invention, less than about 4000 ppm peracid (e.g. mixed peracid actives—total peracid actives), preferably less than about 2000 ppm, preferably less than about 1750 ppm, and more preferably from about 1000 ppm to about 1700 ppm peracid are employed in a post-equilibrium mixed peroxycarboxylic acid composition.

Each of the compositions can be formulated by combining each of the listed ingredients in a pre-equilibrium composition to generate the mixed peroxycarboxylic acid compositions of the invention. The peroxycarboxylic acid compositions are formulated to provide an equilibrium composition, wherein the peracid exists in equilibrium with its corresponding carboxylic acid and the hydrogen peroxide oxidizing agent.

The compositions of the invention may be slightly water insoluble at a use dilution and/or RTU formulation. In an exemplary embodiment of the invention employing peracetic acid and peroctanoic acid, the high acetic acid level in the concentrate form keeps the octanoic acid and the esters solubilized. Upon use dilution, there is not enough acetic acid to hold them in a solution, resulting in the decrease in solubility in a use solution. In an additional aspect of the invention, the inclusion of PSOA assists to provide increased solubility at use solutions. Beneficially, the use of PSOA further aids in rinsing away (i.e. not depositing) the less soluble components. In a further beneficial aspect of the invention, the PSO may also aid in allowing the chemistry to penetrate pathogen bio communities.

Typically, the pH of an equilibrium mixture is less than about 1 or about 2, and the pH of a 1% solution of the equilibrium mixture in water is about 2 to about 9, depending on the other components of the 1% solution, and the pH of a use composition can be from about 1 to about 9 depending on the other components. Preferably, compositions according to the invention have a pH less than about 7, or from about 1 to 7. It is to be understood that all ranges and values between these ranges and values are encompassed by the present invention.

The peroxycarboxylic acid compositions of the present invention have at least the same stability as conventional, commercially-available peroxycarboxylic acid compositions. Without being limited to a particular theory of the invention, the use of alcohol to generate esters (and/or esters added to preformed peroxycarboxylic acids) results in an increase in molarity of the resulting peroxycarboxylic acid compositions, which may have a beneficial effect on the stability of the compositions. In some embodiments, the compositions of the present invention are stable for at least about 2 years at room temperature. In further embodiments, the compositions of the present invention are stable for at least about 1 year at room temperature.

In additional embodiments the enhanced mixed peroxycarboxylic acid compositions of the present invention are also considered to be cold stable compositions. As used herein, "cold stable" refers to a composition that will not phase separate at 4° C. (i.e. refrigerated temperature), which represents conditions wherein the solubility of a composition is the most challenged in its concentrate form. Beneficially, according to an aspect of the invention, the compositions of the present invention are cold stable mixed peracids, including embodiments that do not employ a hydrotrope.

Without being limited to a particular theory of the invention, the combination a $C_2$-$C_4$ peroxycarboxylic acid and a $C_8$-$C_{12}$ peroxycarboxylic acid provides sufficient solubility and also promotes the stability of the compositions. Additional suitable mixed peroxycarboxylic acid compositions according to the invention are disclosed herein.

Peroxycarboxylic Acids

A variety of peroxycarboxylic acids may be employed in the compositions according to the invention. According to an embodiment of the invention suitable peroxycarboxylic acids include ester peroxycarboxylic acids, alkyl ester peroxycarboxylic acids, sulfoperoxycarboxylic acids, and/or combinations of several different peroxycarboxylic acids, as described herein. According to an additional embodiment of the invention one or more carboxylic acids may also be used in the compositions disclosed herein.

In an aspect of the invention a combination of more than one peroxycarboxylic acid are employed. In an embodiment, the peroxycarboxylic acid composition includes at least one sulfocarboxylic acid and sulfoperoxycarboxylic acid. In a further embodiment, the peroxycarboxylic acid composition includes at least one sulfocarboxylic acid and sulfoperoxycarboxylic acid, with at least one percarboxylic acid and peroxycarboxylic acid.

Peroxycarboxylic (or percarboxylic acid or peracids) refer synonymously to acids having the general formula $R(CO_3H)_n$. The R group can be saturated or unsaturated as well as substituted or unsubstituted. As described herein, R is an alkyl, aryl alkyl, cycloalkyl, aromatic, heterocyclic, or ester group, such as an alkyl ester group. N is one, two, or three, and named by prefixing the parent acid with peroxy. Ester groups are defined as R groups including organic moieties (such as those listed above for R) and ester moieties. Exemplary ester groups include aliphatic ester groups, such as $R_1OC(O)R_2$, where each of $R_1$ and $R_2$ can be aliphatic, preferably alkyl, groups described above for R. Preferably $R_1$ and $R_2$ are each independently small alkyl groups, such as alkyl groups with 1 to 5 carbon atoms.

As one skilled in the art shall appreciate, peroxycarboxylic acids are not as stable as carboxylic acids, their stability generally increases with increasing molecular weight. Thermal decomposition of these acids can generally proceed by free radical and nonradical paths, by photodecomposition or radical-induced decomposition, or by the action of metal ions or complexes. Percarboxylic acids can be made by the direct, acid catalyzed equilibrium action of hydrogen peroxide with the carboxylic acid, by autoxidation of aldehydes, or from acid chlorides, and hydrides, or carboxylic anhydrides with hydrogen or sodium peroxide.

In some embodiments of the invention at least one peroxycarboxylic acid is employed. Exemplary peroxycarboxylic acids useful in the compositions of the present invention include peroxyformic, peroxyacetic, peroxypropionic, peroxybutanoic, peroxypentanoic, peroxyhexanoic, peroxyheptanoic, peroxyoctanoic, peroxynonanoic, peroxydecanoic, peroxyundecanoic, peroxydodecanoic, peroxylactic, peroxycitric, peroxymaleic, peroxyascorbic, peroxyhydroxyacetic (peroxyglycolic), peroxyoxalic, peroxymalonic, peroxysuccinic, peroxyglutaric, peroxyadipic, peroxypimelic, peroxysuberic, and peroxysebacic acid, and mixtures thereof. Useful peroxycarboxylic acids also include the ester peroxycarboxylic acids described herein and compositions of the present invention including those ester peroxycarboxylic acids. Peroxy forms of carboxylic acids with more than one carboxylate moiety can have one or more of the carboxyl moieties present as peroxycarboxyl moieties. These peroxycarboxylic acids have been found to provide good antimicrobial action with good stability in aqueous mixtures. In a preferred embodiment, the composition of the invention utilizes a combination of several different peroxycarboxylic acids.

In an embodiment, the composition of the invention utilizes a combination of several different peroxycarboxylic acids to provide the enhanced antimicrobial benefits of the present invention. According to one embodiment, the composition includes more than one $C_1$-$C_{22}$ peroxycarboxylic acids. According to one embodiment, the composition includes one or more small $C_2$-$C_4$ peroxycarboxylic acids, one or more large $C_8$-$C_{12}$ peroxycarboxylic acids, one or more ester peroxycarboxylic acids, one or more alkyl ester peroxycarboxylic acids, and/or one or more mono- or di-peroxycarboxylic acid having up to 12 carbon atoms. According to a further embodiment, the peroxycarboxylic acid has from 2 to 12 carbon atoms. According to an embodiment, the peroxycarboxylic acids include peroxyacetic acid (POAA) (or peracetic acid having the formula $CH_3COOOH$) and/or peroxyoctanoic acid (POOA) (or peroctanoic acid having the formula, for example, of n-peroxyoctanoic acid ($CH_3(CH_2)_6COOOH$).

In an embodiment, the composition of the invention includes an ester peroxycarboxylic acid. As used herein, ester peroxycarboxylic acid refers to a molecule having the formula:

R1 and R2 can independently be any of a wide variety of organic groups (e.g. alkyl, linear or cyclic, aromatic or saturated) or substituted organic groups (e.g., with one or more heteroatoms or organic groups). Ester peroxycarboxylic acid can be made using methods typically employed for producing peroxycarboxylic acid, such as incubating the corresponding ester carboxylic acid with an oxidizing agent, e.g., hydrogen peroxide.

Alkyl ester peroxycarboxylic acids useful in this invention include monomethyl monoperoxyoxalic acid, monomethyl monoperoxymalonic acid, monomethyl monoperoxysuccinic acid, monomethyl monoperoxyglutaric acid, monomethyl monoperoxyadipic acid, monomethyl monoperoxypimelic acid, monomethyl monoperoxysuberic acid, and monomethyl monoperoxysebacic acid; mono ethyl monoperoxyoxalic acid, mono ethyl monoperoxymalonic acid, monoethyl monoperoxysuccinic acid, mono ethyl monoperoxyglutaric acid, mono ethyl monoperoxyadipic acid, mono ethyl monoperoxypimelic acid, mono ethyl monoperoxysuberic acid, and monoethyl monoperoxysebacic acid; monopropyl monoperoxyoxalic acid, monopropyl monoperoxymalonic acid, monopropyl monoperoxysuccinic acid, monopropyl monoperoxyglutaric acid, monopropyl monoperoxyadipic acid, monopropyl monoperoxypimelic acid, monopropyl monoperoxysuberic acid, and monopropyl monoperoxysebacic acid, in which propyl can be n- or iso-propyl; and monobutyl monoperoxyoxalic acid, monobutyl monoperoxymalonic acid, monobutyl monoperoxysuccinic acid, monobutyl monoperoxyglutaric acid, monobutyl monoperoxyadipic acid, monobutyl monoperoxypimelic acid, monobutyl monoperoxysuberic acid, and monobutyl monoperoxysebacic acid, in which butyl can be n-, iso-, or t-butyl.

Further description of suitable alkyl ester peroxycarboxylic acids and ester peroxycarboxylic acids according to the invention is included in U.S. Pat. Nos. 7,816,555 and 7,622,606, both entitled "Peroxycarboxylic Acid Compositions with Reduced Odor," hereby expressly incorporated herein in its entirety by reference, including without limitation all drawings and chemical structures contained therein.

In some embodiments of the invention at least one sulfoperoxycarboxylic acid is employed. Sulfoperoxycarboxylic acids, also referred to herein as sulfonated peracids, may also be used according to the invention and are understood to include the peroxycarboxylic acid form of a sulfonated carboxylic acid. The peroxycarboxylic acid chain can be sulfonated at a variety of locations. In some embodiments, the sulfonated peracids of the present invention are mid-chain sulfonated peracids, referring to a peracid compound that includes a sulfonate group attached to a carbon that is at least one carbon (e.g., the three position or further) from the carbon of the percarboxylic acid group in the carbon backbone of the percarboxylic acid chain, wherein the at least one carbon is not in the terminal position. As used herein, the term "terminal position," refers to the carbon on the carbon backbone chain of a percarboxylic acid that is furthest from the percarboxyl group.

According to an embodiment of the invention, sulfoperoxycarboxylic acids have the following general formula:

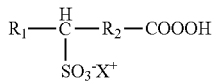

wherein $R_1$ is hydrogen, or a substituted or unsubstituted alkyl group; $R_2$ is a substituted or unsubstituted alkyl group; X is hydrogen, a cationic group, or an ester forming moiety; or salts or esters thereof.

In some embodiments, $R_1$ is a substituted or unsubstituted $C_m$ alkyl group; X is hydrogen a cationic group, or an ester forming moiety; $R_2$ is a substituted or unsubstituted $C_n$ alkyl group; m=1 to 10; n=1 to 10; and m+n is less than 18, or salts, esters or mixtures thereof. In some embodiments, $R_1$ is hydrogen. In other embodiments, $R_1$ is a substituted or unsubstituted alkyl group. In some embodiments, $R_1$ is a substituted or unsubstituted alkyl group that does not include a cyclic alkyl group. In some embodiments, $R_1$ is a substituted alkyl group. In some embodiments, $R_1$ is an unsubstituted $C_1$-$C_9$ alkyl group. In some embodiments, $R_1$ is an unsubstituted $C_7$ or $C_8$ alkyl. In other embodiments, $R_1$ is a substituted $C_8$-$C_{10}$ alkyl group. In some embodiments, $R_1$ is a substituted $C_8$-$C_{10}$ alkyl group is substituted with at least 1, or at least 2 hydroxyl groups. In still yet other embodiments, $R_1$ is a substituted $C_1$-$C_9$ alkyl group. In some embodiments, $R_1$ is a substituted $C_1$-$C_9$ substituted alkyl group is substituted with at least 1 $SO_3H$ group. In other embodiments, $R_1$ is a $C_9$-$C_{10}$ substituted alkyl group. In some embodiments, $R_1$ is a substituted $C_9$-$C_{10}$ alkyl group wherein at least two of the carbons on the carbon backbone form a heterocyclic group. In some embodiments, the heterocyclic group is an epoxide group.

In further embodiments, $R_2$ is a substituted $C_1$-$C_{10}$ alkyl group. In some embodiments, $R_2$ is a substituted $C_8$-$C_{10}$ alkyl. In some embodiments, $R_2$ is an unsubstituted $C_6$-$C_9$ alkyl. In other embodiments, $R_2$ is a $C_8$-$C_{10}$ alkyl group substituted with at least one hydroxyl group. In some embodiments, $R_2$ is a $C_{10}$ alkyl group substituted with at least two hydroxyl groups. In other embodiments, $R_2$ is a $C_8$ alkyl group substituted with at least one $SO_3H$ group. In some embodiments, $R_2$ is a substituted $C_9$ group, wherein at least two of the carbons on the carbon backbone form a heterocyclic group. In some embodiments, the heterocyclic group is an epoxide group. In some embodiments, $R_1$ is a $C_8$-$C_9$ substituted or unsubstituted alkyl, and $R_2$ is a $C_7$-$C_8$ substituted or unsubstituted alkyl.

Additional sulfoperoxycarboxylic acids suitable for use in the peracid compositions of the invention include, for example, the following and/or any salts, esters and mixtures thereof:

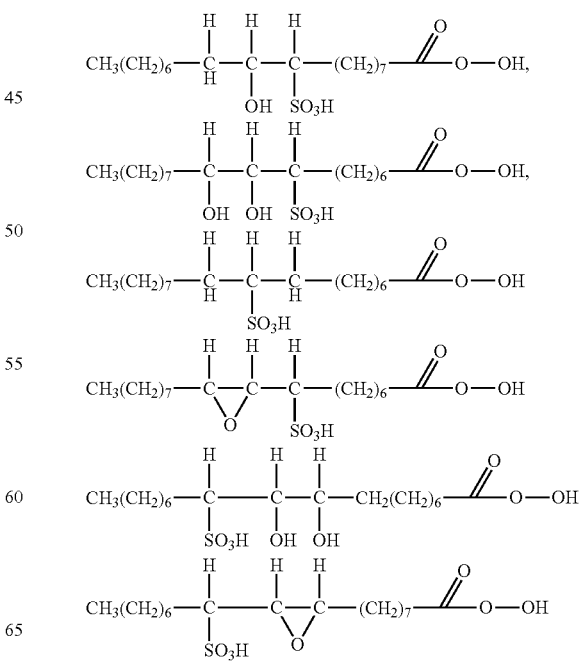

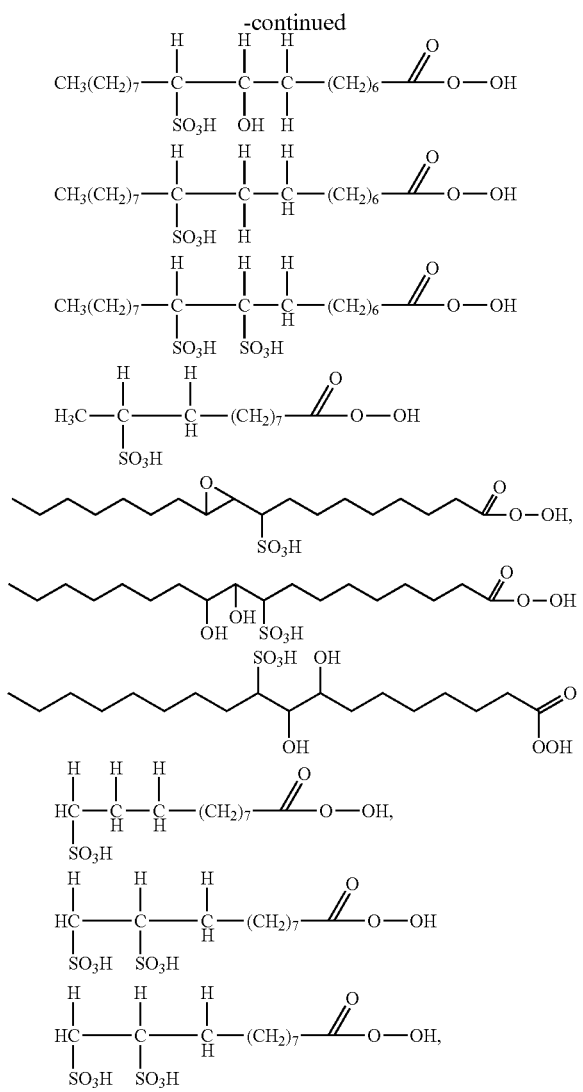

Further description of suitable sulfoperoxycarboxylic acids, and methods of making the same, according to the invention are included in U.S. patent application Ser. Nos. 13/290,355, 12/568,493 and 12/413,179, entitled "Sulfoperoxycarboxylic Acids, Their Preparation and Methods of Use as Bleaching and Antimicrobial Agents," hereby expressly incorporated herein in its entirety by reference, including without limitation all drawings and chemical structures contained therein.

In some embodiments of the invention at least one carboxylic acid is employed in the peroxycarboxylic acid compositions. Generally, carboxylic acids have the formula R—COOH wherein the R can represent any number of different groups including aliphatic groups, alicyclic groups, aromatic groups, heterocyclic groups, and ester groups, such as alkyl ester groups, all of which can be saturated or unsaturated and/or substituted or unsubstituted. Carboxylic acids can have one, two, three, or more carboxyl groups. Preferred ester groups include aliphatic ester groups, such as R1OC(O)R$_2$— where each of R$_1$ and R$_2$ can be aliphatic, preferably alkyl, groups described above for R. Preferably R$_1$ and R$_2$ are each independently small alkyl groups, such as alkyl groups with 1 to 4 carbon atoms.

The composition of the invention can employ carboxylic acids containing as many as 22 carbon atoms. Examples of suitable carboxylic acids include formic, acetic, propionic, butanoic, pentanoic, hexanoic, heptanoic, octanoic, nonanoic, decanoic, undecanoic, dodecanoic, lactic, maleic, ascorbic, citric, hydroxyacetic (glycolic), neopentanoic, neoheptanoic, neodecanoic, oxalic, malonic, succinic, glutaric, adipic, pimelic suberic, and sebacic acid. Examples of suitable alkyl ester carboxylic acids include monomethyl oxalic acid, monomethyl malonic acid, monomethyl succinic acid, monomethyl glutaric acid, monomethyl adipic acid, monomethyl pimelic acid, monomethyl suberic acid, and monomethyl sebacic acid; monoethyl oxalic acid, monoethyl malonic acid, monoethyl succinic acid, monoethyl glutaric acid, monoethyl adipic acid, monoethyl pimelic acid, monoethyl suberic acid, and monoethyl sebacic acid; monopropyl oxalic acid, monopropyl malonic acid, monopropyl succinic acid, monopropyl glutaric acid, monopropyl adipic acid, monopropyl pimelic acid, monopropyl suberic acid, and monopropyl sebacic acid, in which propyl can be n- or isopropyl; and monobutyl oxalic acid, monobutyl malonic acid, monobutyl succinic acid, monobutyl glutaric acid, monobutyl adipic acid, monobutyl pimelic acid, monobutyl suberic acid, and monobutyl sebacic acid, in which butyl can be n-, iso-, or t-butyl.

In some embodiments, the carboxylic acid for use with the compositions of the present invention is a $C_2$ to $C_{12}$ carboxylic acid. In some embodiments, the carboxylic acid for use with the compositions of the present invention is a $C_5$ to $C_{11}$ carboxylic acid. In some embodiments, the carboxylic acid for use with the compositions of the present invention is a $C_1$ to $C_4$ carboxylic acid. Examples of suitable carboxylic acids include, but are not limited to, formic, acetic, propionic, butanoic, pentanoic, hexanoic, heptanoic, octanoic, nonanoic, decanoic, undecanoic, dodecanoic, as well as their branched isomers, lactic, maleic, ascorbic, citric, hydroxyacetic, neopentanoic, neoheptanoic, neodecanoic, oxalic, malonic, succinic, glutaric, adipic, pimelic subric acid, and mixtures thereof. Carboxylic acids that are generally useful include ester carboxylic acids, such as alkyl ester carboxylic acids.

In some embodiments, the compositions of the present invention include a combination of peroxycarboxylic acids, sulfoperoxycarboxylic acids and/or carboxylic acids. According to an embodiment, the compositions of the present invention include at least one sulfoperoxycarboxylic acid and at least one carboxylic and/or percarboxylic acid. In some embodiments, the compositions of the present invention include at least two, at least three, or at least four or more carboxylic and/or peroxycarboxylic acids.

The chemical structures herein, including the peroxycarboxylic acids, are drawn according to the conventional standards known in the art. Thus, where an atom, such as a carbon atom, as drawn appears to have an unsatisfied valency, then that valency is assumed to be satisfied by a hydrogen atom, even though that hydrogen atom is not necessarily explicitly drawn. The structures of some of the compounds of this invention include stereogenic carbon atoms. It is to be understood that isomers arising from such asymmetry (e.g., all enantiomers and diastereomers) are included within the scope of this invention unless indicated otherwise. That is, unless otherwise stipulated, any chiral carbon center may be of either (R)- or (S)-stereochemistry. Such isomers can be obtained in substantially pure form by classical separation techniques and by stereochemically-controlled synthesis. Furthermore, alkenes can include either the E- or Z-geometry, where appropriate. In addition, the compounds of the present invention may exist in unsolvated as well as solvated forms with acceptable solvents such as water, THF, ethanol, and the like. In general, the solvated forms are considered equivalent to the unsolvated forms for the purposes of the present invention.

The amount of peroxycarboxylic acid in use and concentrate compositions can range up to the limits at which the peroxycarboxylic acid can be dissolved or suspended in the composition. Preferably, the peroxycarboxylic acid is present (in a use or concentrate) of a post-equilibrium composition at a concentration from about 0.01 to about 50% by weight, preferably from about 0.1 to about 50% by weight, from about 1 to about 50% by weight and from about 10 to about 50% by weight. Preferably, the carboxylic acid is present (in a use or concentrate) of a pre-equilibrium composition at a concentration from about 0.1 to about 80% by weight, preferably from about 0.1 to about 50% by weight, from about 1 to about 50% by weight. Preferably, the carboxylic acid is present (in a use or concentrate) of a post-equilibrium composition at a concentration from about 0.1 to about 80% by weight, preferably from about 0.1 to about 40% by weight, from about 1 to about 40% by weight. Use compositions can be further diluted according to various embodiments and such dilutions are included within the scope of the invention. It is to be understood that all ranges and values between these ranges and values are encompassed by the present invention.

Making the Peroxycarboxylic Acids

Exemplary methods and apparatus for making peroxycarboxylic acids are disclosed in U.S. Pat. No. 7,547,421 and U.S. patent application Ser. No. 12/430,523, both entitled "Apparatus and Method for Making a Peroxycarboxylic Acid," hereby expressly incorporated herein in its entirety by reference. These and other known methods and apparatus for making the particular peroxycarboxylic acids and/or sulfoperoxycarboxylic acids according to the invention are included within the scope of the invention.

In some embodiments, the starting material for the preparation of the peroxycarboxylic acids of the compositions is a fatty acid, which may also include a sulfonated fatty acid. In some embodiments, the percarboxylic acids of the present invention are formed from commercially available fatty acids. According to some embodiments the percarboxylic acids of the present invention are formed from sulfonated fatty acids. In other embodiments, the compounds of the present invention are formed from commercially available non-sulfonated fatty acids, which can be sulfonated. In some embodiments, the starting fatty acid will be sulfonated prior to conversion to a peroxycarboxylic acid. In other embodiments, the starting fatty acid will be sulfonated at the same time or after the formation of the peroxycarboxylic acid. Sulfonated fatty acids suitable for use in forming compounds of the present invention include, but are not limited to, 11-sulfoundecanoic acid, 10,11-disulfoundecanoic acid, sulfonated oleic acid, sulfonated linoleic acid, sulfonated palmitoleic acid and sulfonated stearic acid.

Depending upon the starting fatty acid for the preparation of the mixed peroxycarboxylic acids of the compositions, a mixture of compounds are included in the compositions of the present invention. For example, according to the embodiment of the invention using a sulfonated oleic acid starting material which may contain more than one form of the sulfonated oleic acid as it is not chemically pure, the formed peroxysulfonated oleic acid can include a mixture of sulfoperoxyacid compounds. According to this embodiment of the invention, the sulfoperoxyacids can be formed using a variety of reaction mechanisms, including for example, direct acid catalyzed equilibrium action of hydrogen peroxide with the starting materials. The sulfonated oleic acid may then be combined with non-sulfonated fatty acids, such as acetic acid and/or octanoic acid.

In some aspects, at ambient conditions, the reaction to make the peroxycarboxylic acid compositions may take a week or more to reach the desirable concentrations of peroxycarboxylic acid at equilibrium. In other aspects conditions can be modified to reach maximum peroxycarboxylic acid compositions within about 60 minutes or within a few hours. One skilled in the art will ascertain the various modifications to the conditions of the peroxycarboxylic acid reactions in order to obtain the desirable concentrations within a particular amount of time.

In certain embodiments of the invention, the peroxycarboxylic acid compositions are made in the presence of the alcohol, rather than using an alcohol adjuvant that is added after forming the peroxycarboxylic acid.

In alternative embodiments of the invention, an ester source is provided to the preformed peroxycarboxylic acid compositions. As one of skill in the art appreciates, there are commercially-available sources of esters that can be provided to an already formed peroxycarboxylic acid composition. For example, ES-1000 is a commercially-available ester product (Ecolab Inc.).

Esters

A variety of esters may be used in the peroxycarboxylic acid compositions according to the invention. The esters are preferably alkyl esters. In a further aspect the esters are preferably ethyl esters. In a further aspect the esters are sparingly soluble esters. A combination of esters may also be employed, such as dimethyl esters. Esters having different concentrations may be employed according to the invention.

In aspects of the invention wherein esters are formed through esterification reactions with an alcohol and the carboxylic acids employed in a pre-equilibrium peroxycarboxylic acid composition, various esters will be formed dependent upon the starting material (e.g. C1-C22 carboxylic acids and alcohols). In an exemplary embodiment of the invention, ethyl acetate and ethyl octanoate are formed in a mixed peroxycarboxylic acid composition.

Any of the esters disclosed herein may also be combined in a mixture of esters for use in the compositions of the invention. Accordingly, the composition may contain one type of ester, or a mixture of two or more esters for inclusion in a preformed peroxycarboxylic acid composition according to the invention.

Alcohols

A variety of alcohols may be used in the peroxycarboxylic acid compositions according to the invention. The alcohols provide various benefits, including removing malodorous, low molecular weight carboxylic acids through esterification. In addition, the alcohols may provide solubilization benefits. The alcohol is preferably a lower chain alcohol such as a $C_2$-$C_6$ or a $C_2$-$C_4$ alcohol. In a preferred aspect, the alcohol is an SDA ethanol (190 proof), such as a tert butyl denaturant ethanol.

Alcohols having different concentrations may be employed according to the invention. The alcohol may also be a mixture of alcohols. Accordingly, the composition may contain one alcohol, or a mixture of two or more alcohols.

Examples of suitable alcohols for use in the peroxycarboxylic acid compositions according to the invention include methanol, ethanol, propanols, butanols, benzyl alcohol, nonanols and the like. The alcohol is preferably ethanol, providing a pleasant, fruity odor and a cost effective solution to the problem solved by the present invention. According to a further embodiment, ethanol provides unreacted residues having a favorable toxicity profile.

According to the present invention, formulation of the peroxycarboxylic acid compounds including an alcohol, such as ethanol, results in a pleasant ester-like odor in the formulation within several hours of adding ethanol and/or the other alcohols. Although not intending to be limited according to a particular theory of the invention, the alcohol results in either significant esterification of the various short chain carboxylic acids or at least a thorough masking of those odors.

The alcohol is preferably present in the pre-equilibrium peracid composition in an amount from about 0.1 wt-% to about 20 wt-%, from about 0.1 wt-% to about 10 wt-%, from about 1 wt-% to about 10 wt-% alcohol, or more preferably from about 1 wt-% to about 5 wt-% alcohol. The amount of alcohol in the peracid compositions according to the invention may vary depending upon the formulation of a concentration or a use solution. In certain embodiments, a concentrate composition may be diluted by a factor of from about 16:1 to about 1000:1, resulting in use concentrations of the alcohol from about 5 ppm to about 1,000 ppm. It is to be understood that all ranges and values between these ranges and values are encompassed by the present invention.

Oxidizing Agents

In some aspects of the invention, the peroxycarboxylic acid compositions include at least one oxidizing agent. When present in the peroxycarboxylic acid compositions, any of a variety of oxidizing agents may be employed, for example, hydrogen peroxide. The oxidizing agent can be present at an amount effective to convert a fatty acid, such as a carboxylic acid or a sulfonated carboxylic acid to a peroxycarboxylic acid or a sulfonated peroxycarboxylic acid. In some embodiments, the oxidizing agent can also have antimicrobial activity. In other embodiments, the oxidizing agent is present in an amount insufficient to exhibit antimicrobial activity.

Examples of inorganic oxidizing agents include the following types of compounds or sources of these compounds, or alkali metal salts including these types of compounds, or forming an adduct therewith: hydrogen peroxide, urea-hydrogen peroxide complexes or hydrogen peroxide donors of: group 1 (IA) oxidizing agents, for example lithium peroxide, sodium peroxide; group 2 (IIA) oxidizing agents, for example magnesium peroxide, calcium peroxide, strontium peroxide, barium peroxide; group 12 (IIB) oxidizing agents, for example zinc peroxide; group 13 (IIIA) oxidizing agents, for example boron compounds, such as perborates, for example sodium perborate hexahydrate of the formula $Na_2[B_2(O_2)_2(OH)_4]6H_2O$ (also called sodium perborate tetrahydrate); sodium peroxyborate tetrahydrate of the formula $Na_2B_2(O_2)_2[(OH)_4]4H_2O$ (also called sodium perborate trihydrate); sodium peroxyborate of the formula $Na_2[B_2(O_2)_2(OH)_{\cdot 4}]$ (also called sodium perborate monohydrate); group 14 (VA) oxidizing agents, for example persilicates and peroxycarbonates, which are also called percarbonates, such as persilicates or peroxycarbonates of alkali metals; group 15 (VA) oxidizing agents, for example peroxynitrous acid and its salts; peroxyphosphoric acids and their salts, for example, perphosphates; group 16 (VIA) oxidizing agents, for example peroxysulfuric acids and their salts, such as peroxymonosulfuric and peroxydisulfuric acids, and their salts, such as persulfates, for example, sodium persulfate; and group VIIa oxidizing agents such as sodium periodate, potassium perchlorate. Other active inorganic oxygen compounds can include transition metal peroxides; and other such peroxygen compounds, and mixtures thereof.

In some embodiments, the compositions of the present invention employ one or more of the inorganic oxidizing agents listed above. Suitable inorganic oxidizing agents include ozone, hydrogen peroxide, hydrogen peroxide adduct, group IIIA oxidizing agent, or hydrogen peroxide donors of group VIA oxidizing agent, group VA oxidizing agent, group VIIA oxidizing agent, or mixtures thereof. Suitable examples of such inorganic oxidizing agents include percarbonate, perborate, persulfate, perphosphate, persilicate, or mixtures thereof.

The peroxycarboxylic acid compositions preferably include a hydrogen peroxide constituent. Beneficially, hydrogen peroxide in combination with the peroxycarboxylic acids provides certain antimicrobial actions against microorganisms. Additionally, hydrogen peroxide can provide an effervescent action which can irrigate any surface to which it is applied. Hydrogen peroxide works with a mechanical flushing action once applied which further cleans the surface. An additional advantage of hydrogen peroxide is the food compatibility of this composition upon use and decomposition. For example, combinations of peroxyacetic acid, peroxyoctanoic acid, and hydrogen peroxide result in acetic acid, octanoic acid, water, and oxygen upon decomposition, all of which are food product compatible and do not adversely affect an apparatus, handling or processing, or other surfaces to which the peroxycarboxylic acid composition is applied.

In some embodiments, the compositions of the present invention include about 0.1 wt-% oxidizing agent to about 80 wt-% oxidizing agent in a pre-equilibrium composition. In other embodiments, the compositions of the present invention include about 1 wt % to about 80 wt % oxidizing agent. In some embodiments, the compositions of the invention include about 10 wt-% to about 75 wt-% oxidizing agent. It is to be understood that all ranges and values between these ranges and values are encompassed by the present invention.

Surfactant

In some aspects of the invention, the peroxycarboxylic acid compositions include at least one surfactant. Surfactants are preferably included in the peroxycarboxylic acid compositions to increase solubility of the peroxycarboxylic acid or to maintain the pH of the composition. According to an embodiment of the invention, the surfactant is a hydrotrope coupler or solubilizer, which can be used to ensure that the composition remains phase stable and in a single highly active aqueous form. Such hydrotrope solubilizers or couplers can be used at concentrations that maintain phase stability but do not result in unwanted compositional interaction.

Surfactants particularly suitable for use with the compositions of the present invention include, but are not limited to, nonionic surfactants, anionic surfactants, amphoteric surfactants and zwitterionic surfactants. Preferably, anionic surfactants are employed with the peracid compositions of the invention. Exemplary surfactants that can be used are commercially available from a number of sources. For a discussion of surfactants, see Kirk-Othmer, Encyclopedia of Chemical Technology, Third Edition, volume 8, pages 900-912.

According to a preferred embodiment of the invention, the surfactant is an acidic anionic surfactant. According to a further embodiment, the surfactant is an antimicrobial agent. Exemplary surfactant, hydrotrope solubilizers include anionic surfactants such as an alkyl sulfate, an aryl sulfonate, an alkyl or alkane sulfonate, a linear alkyl benzene or naphthalene sulfonate, a secondary alkane sulfonate, alkyl ether sulfate or sulfonate, an alkyl phosphate or phosphonate, dialkyl sulfosuccinic acid ester, sugar esters (e.g., sorbitan esters) and a $C_{8-10}$ alkyl glucoside. In additional embodiments, a surfactant may include a sulfonated oleic acid.

In some embodiments, the pre-equilibrium compositions of the present invention includes from about 0.001 wt-% to about 20 wt-% of a surfactant. In other embodiments the compositions of the present invention include from about 0.01 wt-% to about 5 wt-% of a surfactant. In additional embodiments, the post-equilibrium compositions of the present invention include from about 0.00001 wt-% to about 10 wt-% of a surfactant. In further embodiments, the compositions of the present invention include about 10 ppm to about 10,000 ppm of a surfactant. In further embodiments, the compositions of the present invention include about 10 ppm to about 100 ppm of a surfactant. It is to be understood that all ranges and values between these ranges and values are encompassed by the present invention.

Nonionic Surfactants

Suitable nonionic surfactants suitable for use with the compositions of the present invention include alkoxylated surfactants. Suitable alkoxylated surfactants include EO/PO copolymers, capped EO/PO copolymers, alcohol alkoxylates, capped alcohol alkoxylates, mixtures thereof, or the like. Suitable alkoxylated surfactants for use as solvents include EO/PO block copolymers, such as the Pluronic and reverse Pluronic surfactants; alcohol alkoxylates; and capped alcohol alkoxylates, such as Plurafac LF221 and Tegoten EC11; mixtures thereof, or the like.

Semi-Polar Nonionic Surfactants

The semi-polar type of nonionic surface active agents are another class of nonionic surfactant useful in compositions of the present invention. Semi-polar nonionic surfactants include the amine oxides, phosphine oxides, sulfoxides and their alkoxylated derivatives.

Amine oxides are tertiary amine oxides corresponding to the general formula:

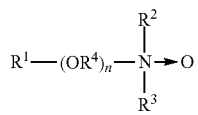

wherein the arrow is a conventional representation of a semi-polar bond; and, $R^1$, $R^2$, and $R^3$ may be aliphatic, aromatic, heterocyclic, alicyclic, or combinations thereof. Generally, for amine oxides of detergent interest, $R^1$ is an alkyl radical of from about 8 to about 24 carbon atoms; $R^2$ and $R^3$ are alkyl or hydroxyalkyl of 1-3 carbon atoms or a mixture thereof; $R^2$ and $R^3$ can be attached to each other, e.g. through an oxygen or nitrogen atom, to form a ring structure; $R^4$ is an alkylene or a hydroxyalkylene group containing 2 to 3 carbon atoms; and n ranges from 0 to about 20. An amine oxide can be generated from the corresponding amine and an oxidizing agent, such as hydrogen peroxide.

Useful water soluble amine oxide surfactants are selected from the octyl, decyl, dodecyl, isododecyl, coconut, or tallow alkyl di-(lower alkyl)amine oxides, specific examples of which are octyldimethylamine oxide, nonyldimethylamine oxide, decyldimethylamine oxide, undecyldimethylamine oxide, dodecyldimethylamine oxide, iso-dodecyldimethyl amine oxide, tridecyldimethylamine oxide, tetradecyldimethylamine oxide, pentadecyldimethylamine oxide, hexadecyldimethylamine oxide, heptadecyldimethylamine oxide, octadecyldimethylaine oxide, dodecyldipropylamine oxide, tetradecyldipropylamine oxide, hexadecyldipropylamine oxide, tetradecyldibutylamine oxide, octadecyldibutylamine oxide, bis(2-hydroxyethyl)dodecylamine oxide, bis (2-hydroxyethyl)-3-dodecoxy-1-hydroxypropylamine oxide, dimethyl-(2-hydroxydodecyl)amine oxide, 3,6,9-trioctadecyldimethylamine oxide and 3-dodecoxy-2-hydroxypropyldi-(2-hydroxyethyl)amine oxide.

Anionic Surfactants

Anionic sulfate surfactants suitable for use in the present compositions include alkyl ether sulfates, alkyl sulfates, the linear and branched primary and secondary alkyl sulfates, alkyl ethoxysulfates, fatty oleyl glycerol sulfates, alkyl phenol ethylene oxide ether sulfates, the $C_5$-$C_{17}$ acyl-N—($C_1$-$C_4$ alkyl) and —N—($C_1$-$C_2$ hydroxyalkyl)glucamine sulfates, and sulfates of alkylpolysaccharides such as the sulfates of alkylpolyglucoside, and the like. Also included are the alkyl sulfates alkyl poly(ethyleneoxy)ether sulfates and aromatic poly(ethyleneoxy)sulfates such as the sulfates or condensation products of ethylene oxide and nonyl phenol (usually having 1 to 6 oxyethylene groups per molecule).

Anionic sulfonate surfactants suitable for use in the present compositions also include alkyl sulfonates, the linear and branched primary and secondary alkyl sulfonates, and the aromatic sulfonates with or without substituents.

Anionic carboxylate surfactants suitable for use in the present compositions include carboxylic acids (and salts), such as alkanoic acids (and alkanoates), ester carboxylic acids (e.g. alkyl succinates), ether carboxylic acids, and the like. Such carboxylates include alkyl ethoxy carboxylates, alkyl aryl ethoxy carboxylates, alkyl polyethoxy polycarboxylate surfactants and soaps (e.g. alkyl carboxyls). Secondary carboxylates useful in the present compositions include those which contain a carboxyl unit connected to a secondary carbon. The secondary carbon can be in a ring structure, e.g. as in p-octyl benzoic acid, or as in alkyl-substituted cyclohexyl carboxylates. The secondary carboxylate surfactants typically contain no ether linkages, no ester linkages and no hydroxyl groups. Further, they typically lack nitrogen atoms in the head-group (amphiphilic portion). Suitable secondary soap surfactants typically contain 11-13 total carbon atoms, although more carbons atoms (e.g., up to 16) can be present. Suitable carboxylates also include acylamino acids (and salts), such as acylgluamates, acyl peptides, sarcosinates (e.g. N-acyl sarcosinates), taurates (e.g. N-acyl taurates and fatty acid amides of methyl tauride), and the like.

Suitable anionic surfactants include alkyl or alkylaryl ethoxy carboxylates of the following formula:

R—O—(CH$_2$CH$_2$O)$_n$(CH$_2$)$_m$—CO$_2$X in which R is a $C_8$ to $C_{22}$ alkyl group or

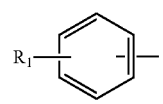

in which $R_1$ is a $C_4$-$C_{16}$ alkyl group; n is an integer of 1-20; m is an integer of 1-3; and X is a counter ion, such as hydrogen, sodium, potassium, lithium, ammonium, or an amine salt such as monoethanolamine, diethanolamine or triethanolamine. In some embodiments, n is an integer of 4 to 10 and m is 1. In some embodiments, R is a $C_8$-$C_{16}$ alkyl group. In some embodiments, R is a $C_{12}$-$C_{14}$ alkyl group, n is 4, and m is 1.

In other embodiments, R is

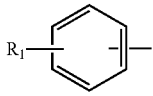

and $R_1$ is a $C_6$-$C_{12}$ alkyl group. In still yet other embodiments, $R_1$ is a $C_9$ alkyl group, n is and m is 1. Such alkyl and alkylaryl ethoxy carboxylates are commercially available. These ethoxy carboxylates are typically available as the acid forms, which can be readily converted to the anionic or salt form.

Amphoteric Surfactants

Amphoteric, or ampholytic, surfactants contain both a basic and an acidic hydrophilic group and an organic hydrophobic group. These ionic entities may be any of anionic or cationic groups described herein for other types of surfactants. A basic nitrogen and an acidic carboxylate group are the typical functional groups employed as the basic and acidic hydrophilic groups. In a few surfactants, sulfonate, sulfate, phosphonate or phosphate provide the negative charge.

Amphoteric surfactants can be broadly described as derivatives of aliphatic secondary and tertiary amines, in which the aliphatic radical may be straight chain or branched and wherein one of the aliphatic substituents contains from about 8 to 18 carbon atoms and one contains an anionic water solubilizing group, e.g., carboxy, sulfo, sulfato, phosphate, or phosphono. Amphoteric surfactants are subdivided into two major classes known to those of skill in the art and described in "Surfactant Encyclopedia" Cosmetics & Toiletries, Vol. 104 (2) 69-71 (1989), which is herein incorporated by reference in its entirety. The first class includes acyl/dialkyl ethylenediamine derivatives (e.g. 2-alkyl hydroxyethyl imidazoline derivatives) and their salts. The second class includes N-alkylamino acids and their salts. Some amphoteric surfactants can be envisioned as fitting into both classes.

Amphoteric surfactants can be synthesized by methods known to those of skill in the art. For example, 2-alkyl hydroxyethyl imidazoline is synthesized by condensation and ring closure of a long chain carboxylic acid (or a derivative) with dialkyl ethylenediamine. Commercial amphoteric surfactants are derivatized by subsequent hydrolysis and ring-opening of the imidazoline ring by alkylation—for example with chloroacetic acid or ethyl acetate. During alkylation, one or two carboxy-alkyl groups react to form a tertiary amine and an ether linkage with differing alkylating agents yielding different tertiary amines.

Exemplary suitable amphoteric surfactants include long chain imidazole derivatives, including carboxymethylated compounds (glycinates) which are frequently are called betaines. Betaines are a special class of amphoteric discussed herein below in the section entitled, Zwitterion Surfactants. These and other amphoteric surfactants are further described in U.S. patent application Ser. No. 12/568,493, entitled "Sulfoperoxycarboxylic Acids, Their Preparation and Methods of Use as Bleaching and Antimicrobial Agents," hereby expressly incorporated herein in its entirety by reference.

Long chain imidazole derivatives having application in the present invention generally have the general formula:

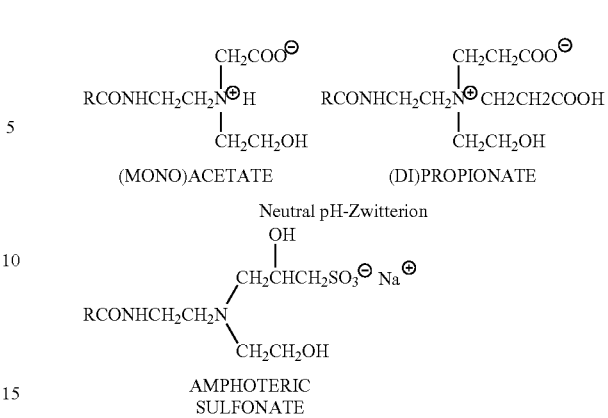

wherein R is an acyclic hydrophobic group containing from about 8 to 18 carbon atoms and M is a cation to neutralize the charge of the anion, generally sodium. Commercially prominent imidazoline-derived amphoterics that can be employed in the present compositions include for example: Cocoamphopropionate, Cocoamphocarboxy-propionate, Cocoamphoglycinate, Cocoamphocarboxy-glycinate, Cocoamphopropyl-sulfonate, and Cocoamphocarboxy-propionic acid. Amphocarboxylic acids can be produced from fatty imidazolines in which the dicarboxylic acid functionality of the amphodicarboxylic acid is diacetic acid and/or dipropionic acid.

The carboxymethylated compounds (glycinates) described herein above frequently are called betaines. Betaines are a special class of amphoteric discussed herein below in the section entitled, Zwitterion Surfactants.

Additionally suitable amphoteric surfactants include long chain N-alkylamino acids which are readily prepared by reaction $RNH_2$, in which R=$C_8$-$C_{18}$ straight or branched chain alkyl, fatty amines with halogenated carboxylic acids. Alkylation of the primary amino groups of an amino acid leads to secondary and tertiary amines. Alkyl substituents may have additional amino groups that provide more than one reactive nitrogen center. Most commercial N-alkylamine acids are alkyl derivatives of beta-alanine or beta-N(2-carboxyethyl) alanine. Examples of commercial N-alkylamino acid ampholytes having application in this invention include alkyl beta-amino dipropionates, $RN(C_2H_4COOM)_2$ and $RNHC_2H_4COOM$. In an embodiment, R can be an acyclic hydrophobic group containing from about 8 to about 18 carbon atoms, and M is a cation to neutralize the charge of the anion.

Suitable amphoteric surfactants include those derived from coconut products such as coconut oil or coconut fatty acid. Additional suitable coconut derived surfactants include as part of their structure an ethylenediamine moiety, an alkanolamide moiety, an amino acid moiety, e.g., glycine, or a combination thereof; and an aliphatic substituent of from about 8 to 18 (e.g., 12) carbon atoms. Such a surfactant can also be considered an alkyl amphodicarboxylic acid. These amphoteric surfactants can include chemical structures represented as: $C_{12}$-alkyl-C(O)—NH—$CH_2$—$CH_2$—$N^+(CH_2$—$CH_2$—$CO_2Na)_2$—$CH_2$—$CH_2$—OH or $C_{12}$-alkyl-C(O)—N(H)—$CH_2$—$CH_2$—$N^+(CH_2$—$CO_2Na)_2$—$CH_2$—$CH_2$—OH.

Disodium cocoampho dipropionate is one suitable amphoteric surfactant and is commercially available under the tradename Miranol™ FBS from Rhodia Inc. (Cranbury, N.J.). Another suitable coconut derived amphoteric surfactant with the chemical name disodium cocoampho diacetate is sold under the tradename Mirataine™ JCHA, also from Rhodia Inc.

A typical listing of amphoteric classes, and species of these surfactants, is given in U.S. Pat. No. 3,929,678 issued to Laughlin and Heuring on Dec. 30, 1975 and further examples are given in "Surface Active Agents and Detergents" (Vol. I and II by Schwartz, Perry and Berch), each of which are hereby expressly incorporated herein in its entirety by reference.

Zwitterionic Surfactants

Zwitterionic surfactants can be thought of as a subset of the amphoteric surfactants and can include an anionic charge. Zwitterionic surfactants can be broadly described as derivatives of secondary and tertiary amines, derivatives of heterocyclic secondary and tertiary amines, or derivatives of quaternary ammonium, quaternary phosphonium or tertiary sulfonium compounds. Typically, a zwitterionic surfactant includes a positive charged quaternary ammonium or, in some cases, a sulfonium or phosphonium ion; a negative charged carboxyl group; and an alkyl group. Zwitterionics generally contain cationic and anionic groups which ionize to a nearly equal degree in the isoelectric region of the molecule and which can develop strong "inner-salt" attraction between positive-negative charge centers. Examples of such zwitterionic synthetic surfactants include derivatives of aliphatic quaternary ammonium, phosphonium, and sulfonium compounds, in which the aliphatic radicals can be straight chain or branched, and wherein one of the aliphatic substituents contains from 8 to 18 carbon atoms and one contains an anionic water solubilizing group, e.g., carboxy, sulfonate, sulfate, phosphate, or phosphonate. Betaine and sultaine surfactants are exemplary zwitterionic surfactants for use herein.

A general formula for these compounds is:

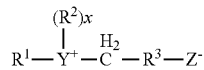

wherein $R^1$ contains an alkyl, alkenyl, or hydroxyalkyl radical of from 8 to 18 carbon atoms having from 0 to 10 ethylene oxide moieties and from 0 to 1 glyceryl moiety; Y is selected from the group consisting of nitrogen, phosphorus, and sulfur atoms; $R^2$ is an alkyl or monohydroxy alkyl group containing 1 to 3 carbon atoms; x is 1 when Y is a sulfur atom and 2 when Y is a nitrogen or phosphorus atom, $R^3$ is an alkylene or hydroxy alkylene or hydroxy alkylene of from 1 to 4 carbon atoms and Z is a radical selected from the group consisting of carboxylate, sulfonate, sulfate, phosphonate, and phosphate groups.

Examples of zwitterionic surfactants having the structures listed above include: 4-[N,N-di(2-hydroxyethyl)-N-octadecylammonio]-butane-1-carboxylate; 5-[S-3-hydroxypropyl-5-hexadecylsulfonio]-3-hydroxypentane-1-sulfate; 3-[P,P-diethyl-P-3,6,9-trioxatetracosanephosphonio]-2-hydroxypropane-1-phosphate; 3-[N,N-dipropyl-N-3-dodecoxy-2-hydroxypropyl-ammonio]-propane-1-phosphonate; 3-(N,N-dimethyl-N-hexadecylammonio)-propane-1-sulfonate; 3-(N,N-dimethyl-N-hexadecylammonio)-2-hydroxy-propane-1-sulfonate; 4-[N,N-di(2(2-hydroxyethyl)-N(2-hydroxydodecyl)ammonio]-butane-1-carboxyl-ate; 3-[S-ethyl-S-(3-dodecoxy-2-hydroxypropyl)sulfonio]-propane-1-phosphat-e; 3-[P,P-dimethyl-P-dodecylphosphonio]-propane-1-phosphonate; and S [N,N-di(3-hydroxypropyl)-N-hexadecylammonio]-2-hydroxy-pentane-1-sulfate. The alkyl groups contained in said detergent surfactants can be straight or branched and saturated or unsaturated.

The zwitterionic surfactant suitable for use in the present compositions includes a betaine of the general structure:

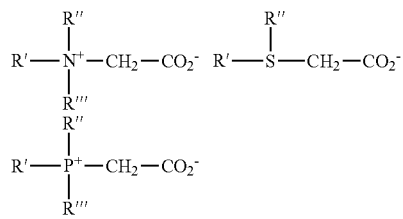

These surfactant betaines typically do not exhibit strong cationic or anionic characters at pH extremes nor do they show reduced water solubility in their isoelectric range. Unlike "external" quaternary ammonium salts, betaines are compatible with anionics. Examples of suitable betaines include coconut acylamidopropyldimethyl betaine; hexadecyl dimethyl betaine; $C_{12-14}$ acylamidopropylbetaine; $C_{8-14}$ acylamidohexyldiethyl betaine; 4-$C_{14-16}$ acylmethylamidodiethylammonio-1-carboxybutane; $C_{16-18}$ acylamidodimethylbetaine; $C_{12-16}$ acylamidopentanediethylbetaine; and $C_{12-16}$ acylmethylamidodimethylbetaine.

Sultaines useful in the present invention include those compounds having the formula $(R(R^1)_2N^+R^2SO^{3-}$, in which R is a $C_6$-$C_{18}$ hydrocarbyl group, each $R^1$ is typically a $C_1$-$C_3$ alkyl, e.g. methyl, and $R^2$ is a $C_1$-$C_6$ hydrocarbyl group, e.g. a $C_1$-$C_3$ alkylene or hydroxyalkylene group.

A typical listing of zwitterionic classes, and species of these surfactants, is given in U.S. Pat. No. 3,929,678 issued to Laughlin and Heuring on Dec. 30, 1975. Further examples are given in "Surface Active Agents and Detergents" (Vol. I and II by Schwartz, Perry and Berch). Each of these references are herein incorporated in their entirety.

Adjuvants—Other Additional Ingredients.

In some embodiments, the compositions of the present invention can include other additional ingredients. Additional ingredients suitable for use with the compositions of the present invention include, but are not limited to, acidulants, stabilizing agents, e.g., chelating agents, sequestrants and/or crystallization inhibitors, buffers, detergents, wetting agents, defoaming agents, thickeners, foaming agents, hydrogen peroxide reducing agents (e.g. catalase enzymes), solidification agents, aesthetic enhancing agents (i.e., colorants, odorants, or perfumes) and other cleaning agents. These additional ingredients can be preformulated with the compositions of the invention or added to the system before, after, or substantially simultaneously with the addition of the compositions of the present invention. Additionally, the compositions can be used in conjunction with one or more conventional cleaning agents, e.g., an alkaline detergent.

Acidulants

In some embodiments, the compositions of the present invention include an acidulant. The acidulant can act as a catalyst for conversion of carboxylic acid to peroxycarboxylic acid or ester formation. The acidulant can be effective to form a concentrate composition with pH of about 1 or less. The acidulant can be effective to form a use composition with pH of about 5, about 5 or less, about 4, about 4 or less, about 3, about 3 or less, about 2, about 2 or less, or the like. In some embodiments, an acidulant can be used to lower the pH of an alkaline cleaning solution to a pH of about 10, about 10 or less, about 9, about 9 or less, about 8, about 8 or less, about 7, about 7 or less, about 6, or about 6 or less. In an embodiment, the acidulant includes an inorganic acid. Suitable inorganic acids include, but are not limited to, sulfuric acid, sodium bisulfate, phosphoric acid, nitric acid, hydrochloric acid. In some embodiments, the acidulant includes an organic acid. Suitable organic acids include, but are not limited to, methane sulfonic acid, ethane sulfonic acid, propane sulfonic acid, butane sulfonic acid, xylene sulfonic acid, benzene sulfonic acid, formic acid, acetic acid, mono, di, or tri-halocarboyxlic acids, picolinic acid, dipicolinic acid, and mixtures thereof. In some embodiments, the compositions of the present invention are free or substantially free of a phosphorous based acid.

In some embodiments, acidulant selected can also function as a stabilizing agent. Thus, the compositions of the present invention can be substantially free of an additional stabilizing agent.

In certain embodiments, the present composition includes about 0.5 to about 80 wt-% acidulant, about 1 to about 50 wt-%, about 5 to about 30 wt-% acidulant, or about 7 to about 14 wt-% acidulant. It is to be understood that all values and ranges between these values and ranges are encompassed by the compositions of the present invention.

Stabilizing Agents

In some embodiments, the compositions of the present invention include one or more stabilizing agents. The stabilizing agents can be used, for example, to stabilize the peracid and hydrogen peroxide and prevent the premature oxidation of this constituent within the composition of the invention. In some embodiments, an acidic stabilizing agent can be used. Thus, in some embodiments, the compositions of the present invention can be substantially free of an additional acidulant. Suitable stabilizing agents include, for example, chelating agents or sequestrants. Suitable sequestrants include, but are not limited to, organic chelating compounds that sequester metal ions in solution, particularly transition metal ions. Such sequestrants include organic amino- or hydroxy-polyphosphonic acid complexing agents (either in acid or soluble salt forms), carboxylic acids (e.g., polymeric polycarboxylate), hydroxycarboxylic acids, aminocarboxylic acids, or heterocyclic carboxylic acids, e.g., pyridine-2,6-dicarboxylic acid (dipicolinic acid).

In some embodiments, the compositions of the present invention include dipicolinic acid as a stabilizing agent. Compositions including dipicolinic acid can be formulated to be free or substantially free of phosphorous. It has also been observed that the inclusion of dipicolinic acid in a composition of the present invention aids in achieving the phase stability of the compositions, compared to other conventional stabilizing agents, i.e. 1-hydroxy ethylidene-1,1-diphosphonic acid ($CH_3C(PO_3H_2)_2OH$) (HEDP).

In other embodiments, the sequestrant can be or include phosphonic acid or phosphonate salt. Suitable phosphonic acids and phosphonate salts include HEDP; ethylenediamine tetrakis methylenephosphonic acid (EDTMP); diethylenetriamine pentakis methylenephosphonic acid (DTPMP); cyclohexane-1,2-tetramethylene phosphonic acid; amino[tri(methylene phosphonic acid)]; (ethylene diamine [tetramethylene-phosphonic acid)]; 2-phosphene butane-1,2,4-tricarboxylic acid; or salts thereof, such as the alkali metal salts, ammonium salts, or alkyloyl amine salts, such as mono, di, or tetra-ethanolamine salts; picolinic, dipicolinic acid or mixtures thereof. In some embodiments, organic phosphonates, e.g., HEDP are included in the compositions of the present invention.

Commercially available food additive chelating agents include phosphonates sold under the trade name DEQUEST® including, for example, 1-hydroxyethylidene-1,1-diphosphonic acid, available from Monsanto Industrial Chemicals Co., St. Louis, Mo., as DEQUEST® 2010; amino (tri(methylenephosphonic acid)), ($N[CH_2 2PO_3H_2]_3$), available from Monsanto as DEQUEST® 2000; ethylenediamine [tetra(methylenephosphonic acid)] available from Monsanto as DEQUEST® 2041; and 2-phosphonobutane-1,2,4-tricarboxylic acid available from Mobay Chemical Corporation, Inorganic Chemicals Division, Pittsburgh, Pa., as Bayhibit AM.

The sequestrant can be or include aminocarboxylic acid type sequestrant. Suitable aminocarboxylic acid type sequestrants include the acids or alkali metal salts thereof, e.g., amino acetates and salts thereof. Suitable aminocarboxylates include N-hydroxyethylaminodiacetic acid; hydroxyethylenediaminetetraacetic acid, nitrilotriacetic acid (NTA); ethylenediaminetetraacetic acid (EDTA); N-hydroxyethyl-ethylenediaminetriacetic acid (HEDTA); diethylenetriaminepentaacetic acid (DTPA); and alanine-N, N-diacetic acid; and the like; and mixtures thereof.

The sequestrant can be or include a polycarboxylate. Suitable polycarboxylates include, for example, polyacrylic acid, maleic/olefin copolymer, acrylic/maleic copolymer, polymethacrylic acid, acrylic acid-methacrylic acid copolymers, hydrolyzed polyacrylamide, hydrolyzed polymethacrylamide, hydrolyzed polyamide-methacrylamide copolymers, hydrolyzed polyacrylonitrile, hydrolyzed polymethacrylonitrile, hydrolyzed acrylonitrile-methacrylonitrile copolymers, polymaleic acid, polyfumaric acid, copolymers of acrylic and itaconic acid, phosphino polycarboxylate, acid or salt forms thereof, mixtures thereof, and the like.

In certain embodiments, the present composition includes about 0.01 to about 10 wt-% stabilizing agent, about 0.4 to about 4 wt-% stabilizing agent, about 0.6 to about 3 wt-% stabilizing agent, about 1 to about 2 wt-% stabilizing agent. It is to be understood that all values and ranges within these values and ranges are encompassed by the present invention.

Wetting or Defoaming Agents

Also useful in the compositions of the invention are wetting and defoaming agents. Wetting agents function to increase the surface contact or penetration activity of the antimicrobial composition of the invention. Wetting agents which can be used in the composition of the invention include any of those constituents known within the art to raise the surface activity of the composition of the invention.

Generally, defoamers which can be used in accordance with the invention include silica and silicones; aliphatic acids or esters; alcohols; sulfates or sulfonates; amines or amides; halogenated compounds such as fluorochlorohydrocarbons; vegetable oils, waxes, mineral oils as well as their sulfonated or sulfated derivatives; fatty acids and/or their soaps such as alkali, alkaline earth metal soaps; and phosphates and phosphate esters such as alkyl and alkaline diphosphates, and tributyl phosphates among others; and mixtures thereof.

In some embodiments, the compositions of the present invention can include antifoaming agents or defoamers which are of food grade quality given the application of the method of the invention. To this end, one of the more effective antifoaming agents includes silicones. Silicones such as dimethyl silicone, glycol polysiloxane, methylphenol polysiloxane, trialkyl or tetralkyl silanes, hydrophobic silica defoamers and mixtures thereof can all be used in defoaming applications. Commercial defoamers commonly available include silicones such as Ardefoam® from Armour Industrial Chemical Company which is a silicone bound in an organic emulsion; Foam Kill® or Kresseo® available from Kirusable Chemical Company which are silicone and non-silicone type defoamers as well as silicone esters; and Anti-Foam A® and DC-200 from Dow Corning Corporation which are both food grade type silicones among others. These defoamers can be present at a concentration range from about 0.01 wt-% to 20 wt-%, from about 0.01 wt-% to 5 wt-%, or from about 0.01 wt-% to about 1 wt-%. It is to be understood that all values and ranges within these values and ranges are encompassed by the present invention.

Thickening or Gelling Agents

The compositions of the present invention can include any of a variety of known thickeners. Suitable thickeners include natural gums such as xanthan gum, guar gum, or other gums from plant mucilage; polysaccharide based thickeners, such as alginates, starches, and cellulosic polymers (e.g., carboxymethyl cellulose); polyacrylates thickeners; and hydrocolloid thickeners, such as pectin. In an embodiment, the thickener does not leave contaminating residue on the surface of an object. For example, the thickeners or gelling agents can be compatible with food or other sensitive products in contact areas. Generally, the concentration of thickener employed in the present compositions or methods will be dictated by the desired viscosity within the final composition. However, as a general guideline, the viscosity of thickener within the present composition ranges from about 0.1 wt-% to about 5 wt-%, from about 0.1 wt-% to about 1.0 wt-%, or from about 0.1 wt-% to about 0.5 wt-%. It is to be understood that all values and ranges within these values and ranges are encompassed by the present invention.

Solidification Agent

The present compositions can include a solidification agent, which can participate in maintaining the compositions in a solid form. In some embodiments, the solidification agent can form and/or maintain the composition as a solid. In other embodiments, the solidification agent can solidify the composition without unacceptably detracting from the eventual release of the sulfonated peroxycarboxylic acid. The solidification agent can include, for example, an organic or inorganic solid compound having a neutral inert character or making a functional, stabilizing or detersive contribution to the present composition. Suitable solidification agents include solid polyethylene glycol (PEG), solid polypropylene glycol, solid EO/PO block copolymer, amide, urea (also known as carbamide), nonionic surfactant (which can be employed with a coupler), anionic surfactant, starch that has been made water-soluble (e.g., through an acid or alkaline treatment process), cellulose that has been made water-soluble, inorganic agent, poly(maleic anhydride/methyl vinyl ether), polymethacrylic acid, other generally functional or inert materials with high melting points, mixtures thereof, and the like.

Suitable glycol solidification agents include a solid polyethylene glycol or a solid polypropylene glycol, which can, for example, have molecular weight of about 1,400 to about 30,000. In certain embodiments, the solidification agent includes or is solid PEG, for example PEG 1500 up to PEG 20,000. In certain embodiments, the PEG includes PEG 1450, PEG 3350, PEG 4500, PEG 8000, PEG 20,000, and the like. Suitable solid polyethylene glycols are commercially available from Union Carbide under the tradename CARBO-WAX™.

Suitable amide solidification agents include stearic monoethanolamide, lauric diethanolamide, stearic diethanolamide, stearic monoethanol amide, cocodiethylene amide, an alkylamide, mixtures thereof, and the like. In an embodiment, the present composition can include glycol (e.g., PEG) and amide.

Suitable nonionic surfactant solidification agents include nonylphenol ethoxylate, linear alkyl alcohol ethoxylate, ethylene oxide/propylene oxide block copolymer, mixtures thereof, or the like. Suitable ethylene oxide/propylene oxide block copolymers include those sold under the Pluronic tradename (e.g., Pluronic 108 and Pluronic F68) and commercially available from BASF Corporation. In some embodiments, the nonionic surfactant can be selected to be solid at room temperature or the temperature at which the composition will be stored or used. In other embodiments, the nonionic surfactant can be selected to have reduced aqueous solubility in combination with the coupling agent. Suitable couplers that can be employed with the nonionic surfactant solidification agent include propylene glycol, polyethylene glycol, mixtures thereof, or the like.

Suitable anionic surfactant solidification agents include linear alkyl benzene sulfonate, alcohol sulfate, alcohol ether sulfate, alpha olefin sulfonate, mixtures thereof, and the like. In an embodiment, the anionic surfactant solidification agent is or includes linear alkyl benzene sulfonate. In an embodiment, the anionic surfactant can be selected to be solid at room temperature or the temperature at which the composition will be stored or used.

Suitable inorganic solidification agents include phosphate salt (e.g., alkali metal phosphate), sulfate salt (e.g., magnesium sulfate, sodium sulfate or sodium bisulfate), acetate salt (e.g., anhydrous sodium acetate), Borates (e.g., sodium borate), Silicates (e.g., the precipitated or fumed forms (e.g., Sipernat 50® available from Degussa), carbonate salt (e.g., calcium carbonate or sodium carbonate or their lower hydrates), other known hydratable compounds, mixtures thereof, and the like. In an embodiment, the inorganic solidification agent can include organic phosphonate compound and carbonate salt, such as an E-Form composition.

In some embodiments, the compositions of the present invention can include any agent or combination of agents that provide a requisite degree of solidification and aqueous solubility can be included in the present compositions. In other embodiments, increasing the concentration of the solidification agent in the present composition can tend to increase the hardness of the composition. In yet other embodiments, decreasing the concentration of solidification agent can tend to loosen or soften the concentrate composition.

In some embodiments, the solidification agent can include any organic or inorganic compound that imparts a solid character to and/or controls the soluble character of the present composition, for example, when placed in an aqueous environment. For example, a solidifying agent can provide controlled dispensing if it has greater aqueous solubility compared to other ingredients in the composition. Urea can be one such solidification agent. By way of further example, for systems that can benefit from less aqueous solubility or a slower rate of dissolution, an organic nonionic or amide hardening agent may be appropriate.

In some embodiments, the compositions of the present invention can include a solidification agent that provides for convenient processing or manufacture of the present composition. For example, the solidification agent can be selected to form a composition that can harden to a solid form under ambient temperatures of about 30 to about 50° C. after mixing ceases and the mixture is dispensed from the mixing system, within about 1 minute to about 3 hours, or about 2 minutes to about 2 hours, or about 5 minutes to about 1 hour.

The compositions of the present invention can include solidification agent at any effective amount. The amount of solidification agent included in the present composition can vary according to the type of composition, the ingredients of the composition, the intended use of the composition, the quantity of dispensing solution applied to the solid composition over time during use, the temperature of the dispensing solution, the hardness of the dispensing solution, the physical size of the solid composition, the concentration of the other ingredients, the concentration of the cleaning agent in the composition, and other like factors. Suitable amounts can include about 1 to about 99 wt-%, about 1.5 to about 85 wt-%, about 2 to about 80 wt-%, about 10 to about 45 wt-%, about 15% to about 40 wt-%, about 20% to about 30 wt-%, about 30% to about 70 wt-%, about 40% to about 60 wt-%, up to about 50 wt-%, about 40% to about 50 wt-%. It is to be understood that all values and ranges within these values and ranges are encompassed by the present invention.

Carrier

In some embodiments, the compositions of the present invention include a carrier. The carrier provides a medium which dissolves, suspends, or carries the other components of the composition. For example, the carrier can provide a medium for solubilization, suspension, or production of a sulfonated peroxycarboxylic acid and for forming an equilibrium mixture. The carrier can also function to deliver and wet the composition of the invention on an object. To this end, the carrier can contain any component or components that can facilitate these functions.

In some embodiments, the carrier includes primarily water which can promote solubility and work as a medium for reaction and equilibrium. The carrier can include or be primarily an organic solvent, such as simple alkyl alcohols, e.g., ethanol, isopropanol, n-propanol, benzyl alcohol, and the like. Polyols are also useful carriers, including glycerol, sorbitol, and the like.

Suitable carriers include glycol ethers. Suitable glycol ethers include diethylene glycol n-butyl ether, diethylene glycol n-propyl ether, diethylene glycol ethyl ether, diethylene glycol methyl ether, diethylene glycol t-butyl ether, dipropylene glycol n-butyl ether, dipropylene glycol methyl ether, dipropylene glycol ethyl ether, dipropylene glycol propyl ether, dipropylene glycol tert-butyl ether, ethylene glycol butyl ether, ethylene glycol propyl ether, ethylene glycol ethyl ether, ethylene glycol methyl ether, ethylene glycol methyl ether acetate, propylene glycol n-butyl ether, propylene glycol ethyl ether, propylene glycol methyl ether, propylene glycol n-propyl ether, tripropylene glycol methyl ether and tripropylene glycol n-butyl ether, ethylene glycol phenyl ether (commercially available as DOWANOL EPH™ from Dow Chemical Co.), propylene glycol phenyl ether (commercially available as DOWANOL PPH™ from Dow Chemical Co.), and the like, or mixtures thereof. Additional suitable commercially available glycol ethers (all of which are available from Union Carbide Corp.) include Butoxyethyl PROPASOL™, Butyl CARBITOL™ acetate, Butyl CARBITOL™, Butyl CELLOSOLVE™ acetate, Butyl CELLOSOLVE™, Butyl DIPROPASOL™, Butyl PROPASOL™, CARBITOL™ PM-600, CARBITOL™ Low Gravity, CELLOSOLVE™ acetate, CELLOSOLVE™, Ester EEP™, FILMER IBT™, Hexyl CARBITOL™, Hexyl CELLOSOLVE™, Methyl CARBITOL™, Methyl CELLOSOLVE™ acetate, Methyl CELLOSOLVE™, Methyl DIPROPASOL™, Methyl PROPASOL™ acetate, Methyl PROPASOL™, Propyl CARBITOL™, Propyl CELLOSOLVE™, Propyl DIPROPASOL™ and Propyl PROPASOL™.

In some embodiments, the carrier makes up a large portion of the composition of the invention and may be the balance of the composition apart from the sulfonated peroxycarboxylic acid, oxidizing agent, additional ingredients, and the like. The carrier concentration and type will depend upon the nature of the composition as a whole, the environmental storage, and method of application including concentration of the sulfonated peroxycarboxylic acid, among other factors. Notably the carrier should be chosen and used at a concentration which does not inhibit the efficacy of the peroxycarboxylic acid composition and its intended use, e.g., bleaching, sanitizing, disinfecting.

In certain embodiments, the present composition includes about 5 to about 90 wt-% carrier, about 10 to about 80 wt-% carrier, about 20 to about 60 wt-% carrier, or about 30 to about 40 wt-% carrier. It is to be understood that all values and ranges between these values and ranges are encompassed by the present invention.

Use Compositions

The peroxycarboxylic acid compositions of the present invention include both concentrate compositions and use compositions. For example, a concentrate composition can be diluted, for example with water, to form a use composition. In an embodiment, a concentrate composition can be diluted to a use solution before to application to an object. Primarily for reasons of economics, the concentrate can be marketed and an end user can dilute the concentrate with water or an aqueous diluent to a use solution.

The level of active components in the concentrate composition is dependent on the intended dilution factor and the desired activity of the sulfonated peroxycarboxylic acid compound. Generally, a dilution of about 1 fluid ounce to about 10 gallons of water to about 10 fluid ounces to about 1 gallon of water is used for aqueous compositions of the present invention. In some embodiments, higher use dilutions can be employed if elevated use temperature or extended exposure time (greater than 30 seconds) can be employed. In the typical use locus, the concentrate is diluted with a major proportion of water using commonly available tap or service water mixing the materials at a dilution ratio of about 3 to about 40 ounces of concentrate per 100 gallons of water.

In some embodiments, such as use in laundry applications, the concentrated compositions can be diluted at a dilution ratio of about 0.1 g/L to about 100 g/L concentrate to diluent, about 0.5 g/L to about 10.0 g/L concentrate to diluent, about 1.0 g/L to about 4.0 g/L concentrate to diluent, or about 1.0 g/L to about 2.0 g/L concentrate to diluent. In other embodiments, a use composition can include about 0.01 to about 10 wt-% of a concentrate composition and about 90 to about 99.99 wt-% diluent; or about 0.1 to about 1 wt-% of a concentrate composition and about 99 to about 99.9 wt-% diluent. Amounts of an ingredient in a use composition can be calculated from the amounts listed above for concentrate compositions and these dilution factors.

As one skilled in the art shall appreciate based on the disclosure of the present invention, the reduced-odor and enhanced antimicrobial compositions of the invention can be formulated as a liquid concentrate composition and/or use compositions. The peracid compositions of the present invention can also be formulated as a gel, an aerosol, a gas, a wax, a solid, or a powder, or as a solution or suspension containing such a composition.

Methods of Use Employing Peracid Compositions

The present invention includes methods employing the enhanced antimicrobial peracid compositions. According to one embodiment of the invention, the methods employ the antimicrobial or bleaching activity of the peracid of the compositions. The compositions of the present invention can be used as antimicrobial or bleaching compositions for a variety of substrates and surfaces, e.g., textiles and hard surfaces. The compositions of the present invention can also be used as antimicrobial, disinfectant and/or sanitizer compositions. The compositions of the present invention can also be used for production of polymers, including for example, epoxides. The compositions of the present invention can further be used in pulp and paper bleaching methods having improved odors for the manufacturing methods.

In an aspect of the invention, the enhanced antimicrobial peracid compositions employing a single peracid species provide at least substantially similar cleaning and/or antimicrobial performance in comparison to peracid compositions that do not employ an alcohol for the esterification reaction (and/or esters added to preformed peroxycarboxylic acids) according to the invention.

In a further aspect of the invention, the enhanced antimicrobial peracid compositions employing a combination of more than one peroxycarboxylic acid (i.e. mixed peracids) and the esters according to the present invention provide improved cleaning and/or antimicrobial performance over conventional peracid compositions.

The compositions may be used for various applications, e.g., food contact sanitizing, hard surface disinfection, and textile disinfection. In some embodiments, compositions containing compounds of the present invention can be multipurpose. That is, the compositions of the present invention can, for example, act as both antimicrobials and bleaches. The compositions of the present invention can further act as disinfection, a combination of disinfection and cleaning, virucidal treatment and/or fungicidal treatment.

According to an embodiment of the invention, a method for reducing a microbial population on a variety of surfaces is provided. The methods according to the invention can operate on an object, surface, or the like, by contacting the object or surface with the enhanced antimicrobial peracid compositions of the invention. As one skilled in the art shall ascertain based upon the disclosure of the present invention, contacting can include any of numerous methods for applying a composition, such as spraying the composition, immersing the object in the composition, foam or gel treating the object with the composition, or a combination thereof.

The peracid compositions of the invention can be used for a variety of domestic or industrial applications. In an embodiment, the peracid compositions can be used at manufacturing or processing sites handling foods and plant species. In further embodiments the compositions can be employed for cleaning or sanitizing food processing equipment or materials; sanitizing food contact and nonfood contact hard surfaces, including as a delivery agent of available oxygen; aseptic and ESL bottle rinse applications; conveyor treatments; foam sanitizing for nonfood contact surfaces; fogging sanitization for rooms; nonfood contact packaging equipment; bacteriophage control when applied to pre-cleaned surfaces; sterilization of manufacturing, filling, and packaging equipment in aseptic processes; disinfecting pharmaceutical and cosmetic surfaces; poultry house disinfection; farm premise disinfection; antimicrobial treatment of water filters, reverse osmosis (RO) and ultra-filtration (UF) membrane systems; boosters for alkaline detergents to clean food processing equipment; boosters for acid detergents to clean food processing equipment; sanitizing of hatching eggs, coops, trucks, crates (poultry); food storage facilities; anti-spoilage air circulation systems; refrigeration and cooler equipment; beverage chillers and warmers, blanchers, cutting boards, third sink areas, and meat chillers or scalding devices; and the like.

In some aspects, the peracid compositions of the present invention are useful in the cleaning or sanitizing of containers (including aseptic techniques), processing facilities, or equipment in the food service or food processing industries. The compounds and compositions have particular value for use on food packaging materials and equipment, and especially for cold or hot aseptic packaging. Examples of process facilities in which the compound of the invention can be employed include a milk line dairy, a continuous brewing system, food processing lines such as pumpable food systems and beverage lines, etc. Food service wares can be disinfected with the compound of the invention. For example, the compounds can also be used on or in ware wash machines, low temperature ware wash machines, dishware, bottle washers, bottle chillers, warmers, third sink washers, cutting areas (e.g., water knives, slicers, cutters and saws) and egg washers. Particular treatable surfaces include packaging such as cartons, bottles, films and resins; dish ware such as glasses, plates, utensils, pots and pans; ware wash and low temperature ware wash machines; exposed food preparation area surfaces such as sinks, counters, tables, floors and walls; processing equipment such as tanks, vats, lines, pumps and hoses (e.g., dairy processing equipment for processing milk, cheese, ice cream and other dairy products); and transportation vehicles. Containers include glass bottles, PVC or polyolefin film sacks, cans, polyester, PEN or PET bottles of various volumes (100 ml to 2 liter, etc.), one gallon milk containers, paper board juice or milk containers, etc.

According to a preferred aspect of the invention, the enhanced peracid compositions may be employed for reducing populations of difficult to treat microorganisms commonly found in aseptic cleaning applications, including for example *Bacillus* species, such as *Bacillus atropheaus, Bacillus cereus, Bacillus mycoides, Bacillus subtilis, Bacillus anthracis*, and *Bacillus thuringiensis*. In a particular aspect, the enhanced peracid compositions are particularly effective against *Bacillus atropheaus*.

A particular embodiment suited for use of the enhanced peracid compositions is the field of aseptic cleaning, including both clean in place (CIP) and clean out of place (COP) systems. The enhanced peracid compositions are particularly suitable for use in aseptic cleaning due to their efficacy at lower concentrations and lower temperatures, in comparison to conventional peracid compositions.

As used herein, CIP cleaning techniques are a specific cleaning and disinfection regimen adapted for removing soils from the internal components of tanks, lines, pumps and other process equipment used for processing typically liquid product streams such as beverages, milk, juices, etc. Clean in place cleaning involves passing cleaning solutions through the system without dismantling any system components. The minimum clean-in-place technique involves passing the cleaning solution through the equipment and then resuming normal processing. Alternatively, COP cleaning techniques are a specific cleaning and disinfection regimen adapted for removing soils from interior and exterior surfaces of a wide variety of parts, such as ceramic surfaces, metal surfaces, walls in, wash tanks, soaking vessels, mop buckets, holding tanks, scrub sinks, vehicle parts washers, non-continuous batch washers and systems, and the like.

In some embodiments, the compositions of the present invention are suitable for use as low temperature cleaning, bleaches and/or antimicrobial agents, preferably in the field of CIP and/or COP at temperatures in above 0° C. to about 80° C.

In a further embodiment, the peracid compositions can be employed in a variety of health care, laundry care and/or vehicle care environments. Still further, embodiments for use of the peracid compositions include cooling tower disinfection, biofilm reduction and the treatment of waste water where both its antimicrobial function and its oxidant properties can be utilized.

The present peracid compositions can be employed for reducing the population of pathogenic microorganisms, such as pathogens of humans, animals, and the like. The peracid compositions have activity against a variety of pathogens, including Gram positive (for example, *Listeria monocytogenes* or *Staphylococcus aureus*) and Gram negative (for example, *Escherichia coli* or *Pseudomonas aeruginosa*) bacteria, yeast, molds, bacterial spores, viruses, etc. fungi, molds, bacteria, spores (e.g. endospores), and viruses. Such pathogens can cause a varieties of diseases and disorders.

As a result of the activity of the peracid compositions of the invention, they can be used as or included in products such as sterilants, sanitizers, disinfectants, preservatives, deodorizers, antiseptics, fungicides, germicides, sporicides, virucides, detergents, bleaches, hard surface cleaners, and pre- or post-surgical scrubs.

According to an embodiment of the invention, the peracid compositions are utilized to kill one or more of the food-borne pathogenic bacteria associated with a food product, including, but not limited to, *Salmonella, Campylobacter, Listeria, Escherichia coli*, yeast, and mold. According to further embodiments, the peracid compositions of the present invention are utilized to kill one or more of the pathogenic bacteria associated with a health care surfaces and environments including, but not limited to, *Salmonella, Staphylococcus*, including methicillin resistant *Staphylococcus aureus, Salmonella, Pseudomonas, Escherichia*, mycobacteria, yeast, and mold. In still further embodiments of the present invention, the peracid compositions can kill a wide variety of microorganisms on a food processing surface, on the surface of a food product, in water used for washing or processing of food product, on a health care surface, or in a health care environment.

A concentrate or use concentration of the peracid compositions of the present invention can be applied to or brought into contact with an object or surface by any conventional method or apparatus for applying an antimicrobial or cleaning composition to an object or surface. For example, the object can be wiped with, sprayed with, and/or immersed in the peracid composition, or a use composition made from the peracid composition. Contacting can be manual or by machine which may employ a liquid, gel, aerosol, gas, wax, solid, or powdered peracid compositions according to the invention, or solutions containing these compositions.

According to an embodiment of the invention, upon application of the peracid compositions the object or surface may be moved with mechanical action, preferably agitated, rubbed, brushed, etc. Agitation can be by physical scrubbing, through the action of the spray solution under pressure, through sonication, or by other methods. Agitation increases the efficacy of the spray solution in killing micro-organisms, perhaps due to better exposure of the solution into the crevasses or small colonies containing the micro-organisms.

A sprayed peracid composition can be left on a treated object or surface for a sufficient amount of time to suitably reduce the population of microorganisms, and then rinsed, drained and/or evaporated off the treated object or surface. The present methods require a certain minimal contact time of the peracid composition for occurrence of significant antimicrobial effect. The contact time can vary with concentration of the use composition, method of applying the use composition, temperature of the use composition, amount of soil on the treated object or surface, number of microorganisms on the treated object or surface, type of antimicrobial agent, or the like. Preferably the exposure time is at least about 5 to about 15 seconds.

Immersing an object or surface in a liquid peracid composition can be accomplished by any of a variety of methods known to those of skill in the art. For example, the object can be placed into a tank or bath containing the peracid composition. Alternatively, the object can be transported or processed in a flume of the peracid composition. The washing solution is preferably agitated to increase the efficacy of the solution and the speed at which the solution reduces microorganisms accompanying the object. Agitation can be obtained by conventional methods, including ultrasonics, aeration by bubbling air through the solution, by mechanical methods, such as strainers, paddles, brushes, pump driven liquid jets, or by combinations of these methods. The washing solution can be heated to increase the efficacy of the solution in killing micro-organisms. After the object has been immersed for a time sufficient for the desired antimicrobial effect, the object can be removed from the bath or flume and the peracid composition can be rinsed, drained, or evaporated off the object.

In a further alternative embodiment of the present invention, an object or surface can be treated with a foaming version of the peracid composition. According to an embodiment of the invention, a foam can be prepared by mixing foaming surfactants with the washing solution at time of use. The foaming surfactants can be nonionic, anionic or cationic in nature. Examples of useful surfactant types include, but are not limited to the following: alcohol ethoxylates, alcohol ethoxylate carboxylate, amine oxides, alkyl sulfates, alkyl ether sulfate, sulfonates, quaternary ammonium compounds, alkyl sarcosines, betaines and alkyl amides. The foaming surfactant is typically mixed at time of use with the washing solution. According to an embodiment, use solution levels of the foaming agents is from about 50 ppm to about 2.0 wt-%. Methods of application can include the use of compressed air injected into the mixture, then applied to the object or surface through a foam application device such as a tank foamer or an aspirated wall mounted roamer.

In another alternative embodiment of the present invention, an object or surface can be treated with a thickened or gelled version of the peracid composition. In the thickened or gelled state the washing solution remains in contact with the object or surface for longer periods of time, thus increasing the antimicrobial efficacy. The thickened or gelled solution will also promote adherence of the peracid composition to vertical surfaces. The composition or the washing solution can be thickened or gelled using existing technologies such as: xanthan gum, polymeric thickeners, cellulose thickeners, or the like. The thickeners or gel forming agents can be used either in the concentrated product or mixing with the washing solution, at time of use. Typical use levels of thickeners or gel agents range from about 100 ppm to about 10 wt-%.

Temperatures

The methods and compositions of the present invention can be used at reduced temperatures, e.g., from about ≥0° C. to about ≤80° C., preferably at about ≥40° C. to about ≤60° C., more preferably at temperatures about ≤60° C. or about ≤50° C. The compositions of the invention provide increased cleaning, and in particular disinfecting activity compared to conventional single peracid compositions used at these temperatures.

The ability to use the enhanced peracid compositions according to the invention at reduced temperatures, preferably at about ≤50° C. results in energy and cost savings compared to traditional cleaning techniques that require increased temperatures.

It has also been found that the enhanced peracid compositions of the present invention provide for cleaning and/or disinfecting need reduced amounts of chemistry, compared to conventional cleaning compositions. In some embodiments, the methods of the present invention use significantly less concentrated compositions (based upon active components) than standard single peracid compositions used in conventional cleaning methods. In an aspect of the invention there is at least a 10% reduction in active chemistry use, preferably at least a 20% reduction, more preferably at least a 50% reduction in active chemistry.

Accordingly, the methods of the present invention may effectively remove soil, bleach and/or disinfect surfaces at reduced temperatures, and using a low concentration of chemicals, providing both an energy savings and a reduction in the amount of chemistry consumed per cleaning.

All publications and patent applications in this specification are indicative of the level of ordinary skill in the art to which this invention pertains. All publications and patent applications are herein incorporated by reference to the same extent as if each individual publication or patent application was specifically and individually indicated by reference.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Example 1

A surface disinfectant with ethanol was formulated according to the peroxycarboxylic acid composition of the invention. The baseline formula for the disinfectant (peroxycarboxylic acid composition) is set forth in Table 1.

TABLE 1

| Description | %, w/w |
| --- | --- |
| Biosoft S101 (LAS) | 1-80% |
| Propylene glycol | 1-50% |
| Sulfuric acid, 98% | 1-50% |
| Sulfonated Oleic acid, 50% | 1-50% |
| Hydrogen peroxide, 50% | 1-80% |
| Dipicolinic acid | 1-10% |
| | 100.00% |

Varying amounts of ethanol were added to the baseline formulation as set forth below in Table 2.

TABLE 2

| Sample | Ethanol SDA 40B, % (w/w) | Baseline Formula (of above), % (w/w) | Total, % (w/w) |
| --- | --- | --- | --- |
| EtOH-1 | 1.00 | 99.00 | 100.00 |
| EtOH-2 | 2.00 | 98.00 | 100.00 |
| EtOH-3 | 3.00 | 97.00 | 100.00 |
| EtOH-4 | 4.00 | 96.00 | 100.00 |
| EtOH-5 | 5.00 | 95.00 | 100.00 |

Table 3 shows the percentage peroxysulfonated oleic acid (PSOA), percentage hydrogen peroxide, and percentage available oxygen in each formulation after two weeks of the varying peroxycarboxylic acid compositions stored at about 40° C. for one week and then stored at room temperature for one week. Without the addition of ethanol to the peroxycarboxylic acid composition the composition identified in Table 1 exhibited significant degradation of the peroxycarboxylic acid into short chain carboxylic acids.

TABLE 3

| | Time 2 wks. (40° C. 1 wk. + RT 1 wk.) | | | |
| --- | --- | --- | --- | --- |
| Sample | % EtOH | % PSOA412 | % $H_2O_2$ | % av. $O_2$ |
| EtOH-0 | 0.00 | 6.51 | 14.70 | 7.17 |
| EtOH-1 | 1.00 | 5.90 | 16.43 | 7.96 |
| EtOH-2 | 2.00 | 5.21 | 16.29 | 7.87 |
| EtOH-4 | 4.00 | 4.47 | 17.09 | 8.22 |
| EtOH-5 | 5.00 | 4.18 | 16.94 | 8.13 |

Table 4 shows the percentage peroxysulfonated oleic acid (PSOA), percentage hydrogen peroxide, and percentage available oxygen in each formulation after one year of the varying peroxycarboxylic acid compositions stored at room temperature. The formulation containing no ethanol exhibited significant peracid degradation. Formulations EtOH-1 through EtOH-5 demonstrated stability for at least one year.

The percentage available oxygen in Table 4 is decreased in comparison to the percentage available oxygen in Table 3, demonstrating the increase in degradation of the peroxycarboxylic acids of the composition.

TABLE 4

| | Time ~1 year RT | | | |
| --- | --- | --- | --- | --- |
| Sample | % EtOH | % PSOA412 | % $H_2O_2$ | % av. $O_2$ |
| EtOH-0 | 0.00 | 9.15 | 13.80 | 6.85 |
| EtOH-1 | 1.00 | 9.00 | 12.81 | 6.38 |
| EtOH-2 | 2.00 | 8.12 | 11.21 | 5.59 |
| EtOH-4 | 4.00 | 7.33 | 11.40 | 5.65 |
| EtOH-5 | 5.00 | 7.38 | 11.51 | 5.70 |

Both Tables 3 and 4 show an expected slight decrease in percentage peroxysulfonated oleic acid as a result of replacing peroxycarboxylic acid content with the ethanol. However, no significant degradation of the peroxycarboxylic acid content after up to a year of storage at room temperature demonstrates the unexpected increase in the composition's shelf life. The slight loss in the peracid portion was significantly less than expected.

Example 2

Formulations for mixed peroxycarboxylic acid compositions were analyzed to determine micro efficacy. A mixed peroxycarboxylic acid composition containing persulfonated oleic acid (PSOA), octanoic acid, and acetic acid was analyzed to determine whether improvements in antimicrobial efficacy could be obtained while reducing or removing traditional coupling agents, including hydrotropes for cost-improvements without sacrificing micro efficacy. The ability of acetic acid and other agents, including ethanol, to solubilize octanoic acid was analyzed.

The addition of ethanol to the mixed peroxycarboxylic acid composition solubilized the octanoic acid. In addition, the ethanol formed esters with the octanoic as well as other formula components. Beneficially and unexpectedly, the odor profile of the mixed peroxycarboxylic acid composition was significantly, improved as a result of the formed esters. Observations of the compositions included not only a tolerable odor, but a very pleasant, sweet and fruity character.

The following chemistry compositions listed in Table 5 were tested:

Composition A (a commercially-available benchmark containing 2000 ppm peracetic acid and used a comparison for industry standards), all other formulations tested were diluted based on formula cost comparative to Composition A (e.g. cost dilutions)

Composition B (an ester free (i.e. alcohol-free) formulation)

Composition C (an ester peracid formulation according to invention)

Composition D (an experimental ester free (i.e. alcohol-free) formulation)

Composition E (an experimental ester free (i.e. alcohol-free) formulation)

TABLE 5

| Composition A | |
|---|---|
| Short chain carboxylic acid | 1-50% |
| Chelant | 0.01-5% |
| Oxidizing agent | 1-90% |
| Composition B | |
| Carboxylic acids | 1-50% |
| Chelant | 0.01-5% |
| Acidulant | 1-50% |
| Oxidizing agent | 1-90% |
| Composition C | |
| Carboxylic acids | 1-50% |
| Alcohol | 0.01-20% |
| Acidulant | 1-50% |
| Oxidizing agent | 1-90% |
| Chelant | 0.01-5% |
| Composition D | |
| Carboxylic acids | 1-50% |
| Hydrotrope | 0.01-20% |
| Acidulant | 1-50% |
| Oxidizing agent | 1-90% |
| Chelant | 0.01-5% |
| Composition E | |
| Carboxylic acids | 1-50% |
| Hydrotrope | 0.01-20% |
| Acidulant | 1-50% |

TABLE 5-continued

| Oxidizing agent | 1-90% |
|---|---|
| Chelant | 0.01-5% |
| Defoaming Agent | 0.01-5% |

Microbiological testing was performed on the mixed peroxycarboxylic acid composition according to the invention containing ethanol against *Bacillus atropheaus* according to the follow bottle rinse test procedure.

Culture Preparation: *Bacillus atropheaus* Spore Crop:
1. Inoculate 10 mL of nutrient broth and incubate at 35° C. for 24 hours.
2. Use this culture to inoculate 6 plates of Amended Nutrient Agar. Inoculate with 500 uL and spread over surface of plate.
3. Incubate inverted for 12 days at 35° C.
4. Harvest each plate by rinsing with 10 mL cold sterile water.
5. Centrifuge tubes and resuspend the pellet in cold sterile water. Repeat 4 times.
6. Resuspend at a final volume of 10 mL sterile water per plate.
7. Store at 2-8° C. until ready for use.
8. Dilute the culture 1:50 immediately prior to use.

Bottles were inoculated in a hood, applying one spray of the culture inside the bottle using a travel size hair spray bottle. The bottle was left in the hood overnight, without the blower, to allow the spores to dry.

The bottles were treated to simulate an actual aseptic packaging technique and returned to micro for sampling. Three bottles were treated with each of the following Benchmark composition: 10 sec sterilant spray at 50° C. followed by a 2 second drain, followed by a 5 second rinse at 40° C. followed by a 5 second drain; 2000 ppm POAA. And varying levels of the ester peracid composition but using the same temperatures and contact times. 100 mL of PBDW was added to each bottle and shaken for 1 minute. Then 1.0 and 0.1 mL from each bottle were plated. The contents were poured into a pre-wet analytical filter and vacuum filter. The filters were removed and placed into a 50 mm Petri dish with Tryptic Soy Agar and incubated at 35° C. for 48-72 hours.

The control for the study was conducted by pouring 100 mL PBDW into an inoculated but untreated bottle and shaken for 1 minute. It was then serially diluted and plated.

The peroxycarboxylic acid formulation according to the invention performed as well as if not better than the benchmark chemistry but at a lower use concentration than the benchmark chemistry. The formulations according to the invention having an alcohol capable of forming esters in the peracid formulations demonstrated increased micro efficacy.

As shown in Tables 6A and 7A, the chemistries were tested against *B. atropheaus* with an average inoculum level of 5.7 log (log reduction reported within a margin of error of +/−0.5 log reduction). Composition C outperformed the benchmark along with all other chemistries. The benchmark chemistry (Composition A), a peracetic only chemistry was used a mid range industry standard of 2000 ppm as POAA. As show in Tables 6B and 7B, the control bottles did not receive treatment and indicate where the inoculum level began. (*Denotes "Too Numerous to Count")

TABLE 6A

| | Treatment | Survivors $10^0$ | Survivors $10^{-2}$ | Survivors $10^{-3}$ | Survivors Spores/Bottle | Log Survivors | Log Reduction |
|---|---|---|---|---|---|---|---|
| 1 | Composition A | TNTC* | 97 | 20 | $9.7 \times 10^3$ | 3.99 | 1.72 |
| 2 | Composition A | TNTC | 61 | 10 | $6.1 \times 10^3$ | 3.78 | 1.93 |

TABLE 6A-continued

| | Treatment | Survivors $10^0$ | Survivors $10^{-2}$ | Survivors $10^{-3}$ | Survivors Spores/Bottle | Log Survivors | Log Reduction |
|---|---|---|---|---|---|---|---|
| 3 | Composition A | TNTC | 87 | 10 | $8.7 \times 10^3$ | 3.94 | 1.77 |
| 4 | Composition B | TNTC | 81 | 15 | $8.1 \times 10^3$ | 3.91 | 1.80 |
| 5 | Composition B | TNTC | 45 | 13 | $4.5 \times 10^3$ | 3.65 | 2.06 |
| 6 | Composition B | TNTC | 63 | 6 | $6.3 \times 10^3$ | 3.80 | 1.91 |
| 7 | Composition C | 195 | 74 | 4 | $3.8 \times 10^3$ | 3.58 | 2.13 |
| 8 | Composition C | 140 | 23 | 3 | $1.4 \times 10^2$ | 2.15 | 3.56 |
| 9 | Composition C | 125 | 17 | 2 | $1.2 \times 10^2$ | 2.08 | 3.63 |
| 10 | Composition D | TNTC | 74 | 3 | $7.4 \times 10^3$ | 3.87 | 1.84 |
| 11 | Composition D | TNTC | 165 | 13 | $1.6 \times 10^4$ | 4.20 | 1.51 |
| 12 | Composition D | TNTC | 248 | 26 | $2.5 \times 10^4$ | 4.40 | 1.31 |
| 13 | Composition E | TNTC | 191 | 28 | $1.9 \times 10^4$ | 4.28 | 1.43 |
| 14 | Composition E | TNTC | 175 | 24 | $1.8 \times 10^4$ | 4.26 | 1.45 |
| 15 | Composition E | TNTC | 74 | 11 | $7.4 \times 10^3$ | 3.87 | 1.84 |

TABLE 6B

| | Treatment | Survivors $10^{-4}$ | Survivors $10^{-5}$ | Survivors $10^{-6}$ | Survivors Spores/Bottle | Log Survivors |
|---|---|---|---|---|---|---|
| 16 | Control | 69, 59 | 19, 11 | 0, 2 | $6.4 \times 10^5$ | 5.81 |
| 17 | Control | 44, 50 | 7, 6 | 0, 1 | $4.7 \times 10^5$ | 5.67 |
| 18 | Control | 65, 68 | 14, 14 | 0, 1 | $4.4 \times 10^5$ | 5.64 |

TABLE 7A

| | Treatment | Survivors $10^0$ | Survivors $10^{-2}$ | Survivors $10^{-3}$ | Survivors Spores/Bottle | Log Survivors | Log Reduction |
|---|---|---|---|---|---|---|---|
| 1 | Composition A | 3 | 0 | 0 | 3 | 0.48 | 3.77 |
| 2 | Composition A | 3 | 0 | 0 | 3 | 0.48 | 3.77 |
| 3 | Composition A | 1 | 0 | 0 | 1 | 0.00 | 4.25 |
| 4 | Composition B | 14 | 0 | 0 | 14 | 1.15 | 3.10 |
| 5 | Composition B | 5 | 0 | 0 | 5 | 0.70 | 3.55 |
| 6 | Composition B | 7 | 0 | 0 | 7 | 0.84 | 3.41 |
| 7 | Composition C | 3 | 0 | 0 | 3 | 0.48 | 3.77 |
| 8 | Composition C | 0 | 0 | 0 | <1 | 0.00 | 4.25 |
| 9 | Composition C | 6 | 0 | 0 | 6 | 0.78 | 3.47 |
| 10 | Composition D | TNTC* | 18 | 3 | $1.8 \times 10^3$ | 3.26 | 0.99 |
| 11 | Composition D | TNTC | 13 | 2 | $1.3 \times 10^3$ | 3.11 | 1.14 |
| 12 | Composition D | TNTC | 17 | 4 | $1.7 \times 10^3$ | 3.23 | 1.02 |
| 13 | Composition E | TNTC | 39 | 5 | $3.9 \times 10^3$ | 3.56 | 0.69 |
| 14 | Composition E | TNTC | 45 | 10 | $4.5 \times 10^3$ | 3.65 | 0.60 |
| 15 | Composition E | TNT | 42 | 9 | $4.2 \times 10^3$ | 3.62 | 0.63 |

TABLE 7B

| | Treatment | Survivors $10^{-4}$ | Survivors $10^{-5}$ | Survivors $10^{-6}$ | Survivors Spores/Bottle | Log Survivors |
|---|---|---|---|---|---|---|
| 16 | Control | 2, 3 | 0, 0 | 0, 0 | $2.5 \times 10^4$ | 4.40 |
| 17 | Control | 2, 1 | 0, 0 | 0, 0 | $1.5 \times 10^4$ | 4.18 |
| 18 | Control | 1, 2 | 0, 0 | 0, 0 | $1.5 \times 10^4$ | 4.18 |

Example 3

Additional micro efficacy data was evaluated using the methods of Example 2. A mixed peroxycarboxylic acid composition containing an alcohol for esterification, persulfonated oleic acid (PSOA), octanoic acid, and acetic acid was analyzed against a commercial control product containing acetic acid to determine whether improvements in antimicrobial efficacy obtained using the post-equilibrium compositions of the invention.

As shown in Tables 8, 9 and FIG. 1 the chemistries were tested at the listed ppm active peracids against *B. atropheaus*.

TABLE 8

| | chemistry | concentration | log reduction | average log reduction |
|---|---|---|---|---|
| 1 | Industry Standard | 1988 ppm POAA | 3.67 | 3.58 |
| | Industry Standard | 1988 ppm POAA | 3.28 | |
| | Industry Standard | 1988 ppm POAA | 3.6 | |
| | Industry Standard | 1988 ppm POAA | 3.75 | |
| | Ester Peracid | 1294 ppm total as POAA | 5.64 | 5.7 |
| | Ester Peracid | 1294 ppm total as POAA | 5.56 | |
| | Ester Peracid | 1294 ppm total as POAA | 6.31 | |
| | Ester Peracid | 1294 ppm total as POAA | 5.27 | |
| | Ester Peracid | 1455 ppm total as POAA | 3.8 | 3.79 |
| | Ester Peracid | 1455 ppm total as POAA | 3.67 | |
| | Ester Peracid | 1455 ppm total as POAA | 3.52 | |
| | Ester Peracid | 1455 ppm total as POAA | 4.17 | |

TABLE 8-continued

| chemistry | concentration | log reduction | average log reduction |
|---|---|---|---|
| Ester Peracid | 1554 ppm total as POAA | 6.31 | 5.65 |
| Ester Peracid | 1554 ppm total as POAA | 5.38 | |
| Ester Peracid | 1554 ppm total as POAA | 5.46 | |
| Ester Peracid | 1554 ppm total as POAA | 5.45 | |
| Ester Peracid | 1693 ppm total as POAA | 5.31 | |
| Ester Peracid | 1693 ppm total as POAA | 6.26 | |
| Ester Peracid | 1693 ppm total as POAA | 5.91 | 5.92 |
| Ester Peracid | 1693 ppm total as POAA | 6.21 | |
| 2 Industry Standard | 1990 ppm POAA | 5.14 | 5.15 |
| Industry Standard | 1990 ppm POAA | 5.49 | |
| Industry Standard | 1990 ppm POAA | 5.59 | |
| Industry Standard | 1990 ppm POAA | 4.39 | |
| Ester Peracid | 1124 ppm total as POAA | 1.4 | 1.59 |
| Ester Peracid | 1124 ppm total as POAA | 1.74 | |
| Ester Peracid | 1124 ppm total as POAA | 1.71 | |
| Ester Peracid | 1124 ppm total as POAA | 1.52 | |
| Ester Peracid | 1319 ppm total as POAA | 4.8 | 5 |
| Ester Peracid | 1319 ppm total as POAA | 4.85 | |
| Ester Peracid | 1319 ppm total as POAA | 5.04 | |
| Ester Peracid | 1319 ppm total as POAA | 5.31 | |
| Ester Peracid | 1420 ppm total as POAA | 5.1 | 5.2 |
| Ester Peracid | 1420 ppm total as POAA | 5.45 | |
| Ester Peracid | 1420 ppm total as POAA | 5.39 | |
| Ester Peracid | 1420 ppm total as POAA | 4.87 | |
| Ester Peracid | 1580 ppm total as POAA | 5.59 | 5.98 |
| Ester Peracid | 1580 ppm total as POAA | 6.07 | |
| Ester Peracid | 1580 ppm total as POAA | 6.25 | |
| Ester Peracid | 1580 ppm total as POAA | 6 | |
| 3 Ester Peracid | 1215 ppm total as POAA | | 2.1 |
| Ester Peracid | 1215 ppm total as POAA | | |
| Ester Peracid | 1215 ppm total as POAA | | |
| Ester Peracid | 1215 ppm total as POAA | | |
| Industry Standard | 1151 ppm total as POAA | | tntc |
| Industry Standard | 1151 ppm total as POAA | | |
| Industry Standard | 1151 ppm total as POAA | | |
| Industry Standard | 1151 ppm total as POAA | | |
| Industry Standard | 1341 ppm total as POAA | | 1.98 |
| Industry Standard | 1341 ppm total as POAA | | |
| Industry Standard | 1341 ppm total as POAA | | |
| Industry Standard | 1341 ppm total as POAA | | |
| Industry Standard | 1513 ppm total as POAA | | 2.07 |
| Industry Standard | 1513 ppm total as POAA | | |
| Industry Standard | 1513 ppm total as POAA | | |
| Industry Standard | 1513 ppm total as POAA | | |
| Industry Standard | 1720 ppm total as POAA | | 2.25 |
| Industry Standard | 1720 ppm total as POAA | | |
| Industry Standard | 1720 ppm total as POAA | | |
| Industry Standard | 1720 ppm total as POAA | | |
| Ester Peracid | 1470 ppm total as POAA | | 3.56 |
| Ester Peracid | 1470 ppm total as POAA | | |
| Ester Peracid | 1470 ppm total as POAA | | |
| Ester Peracid | 1470 ppm total as POAA | | |

TABLE 9

| ppm total as POAA | log reduction from Ester peracid | ppm POAA | log reduction from Control |
|---|---|---|---|
| 1294 | 5.7 | 1988 | 3.58 |
| 1455 | 3.79 | | |
| 1544 | 5.65 | | |
| 1693 | 5.92 | | |
| 1124 | 1.59 | 1990 | 5.15 |
| 1319 | 5 | | |
| 1420 | 5.2 | | |
| 1580 | 5.98 | | |
| 1470 | 3.56 | 1151 | 0 |
| 1215 | 2.1 | 1341 | 1.98 |
| | | 1513 | 2.07 |
| | | 1720 | 2.25 |

As shown, the use of the ester peracid compositions according to the invention provide effective micro efficacy with the use of significantly decreased concentration of ppm active peracids. Beneficially, the use of less than 2000 ppm peracid provide aseptic efficacy against difficult to kill microorganisms, including *B. atropheaus*.

Example 4

Micro efficacy testing was conducted using the peracid composition of Example 3 employing a mixed ester peracid composition according to the invention in comparison to industry standard single peracid chemistries used for aseptic bottle rinse. The control was the same a commercially-available peracetic acid composition (i.e. single peracid species). Micro efficacy was conducted on *Bacillus atropheaus*, an endospore forming pathogenic bacteria, representing a difficult to kill microorganism in this industry. Aseptic cleaning requires an effective sporicide achieving a 5 log reduction in microorganism populations.

Testing employed a contact time of the sterilant solution of 10 seconds, delivered at 50° C. at 3 bar. The total contact time was 12 seconds which includes a 2 second dwell time after spraying of the sterilant and before spraying sterile water at 40° C., at a pressure of 3 bar. Then the bottles were allowed to drain for 5 seconds before they were capped and quantified for micro efficacy.

The test conditions mimicked industry practice for aseptic bottle filling, with the exception of delivering the compositions at a lower temperature of 50° C. sterilant solution as opposed to 60° C. currently employed in aseptic methods.

Figure 2:
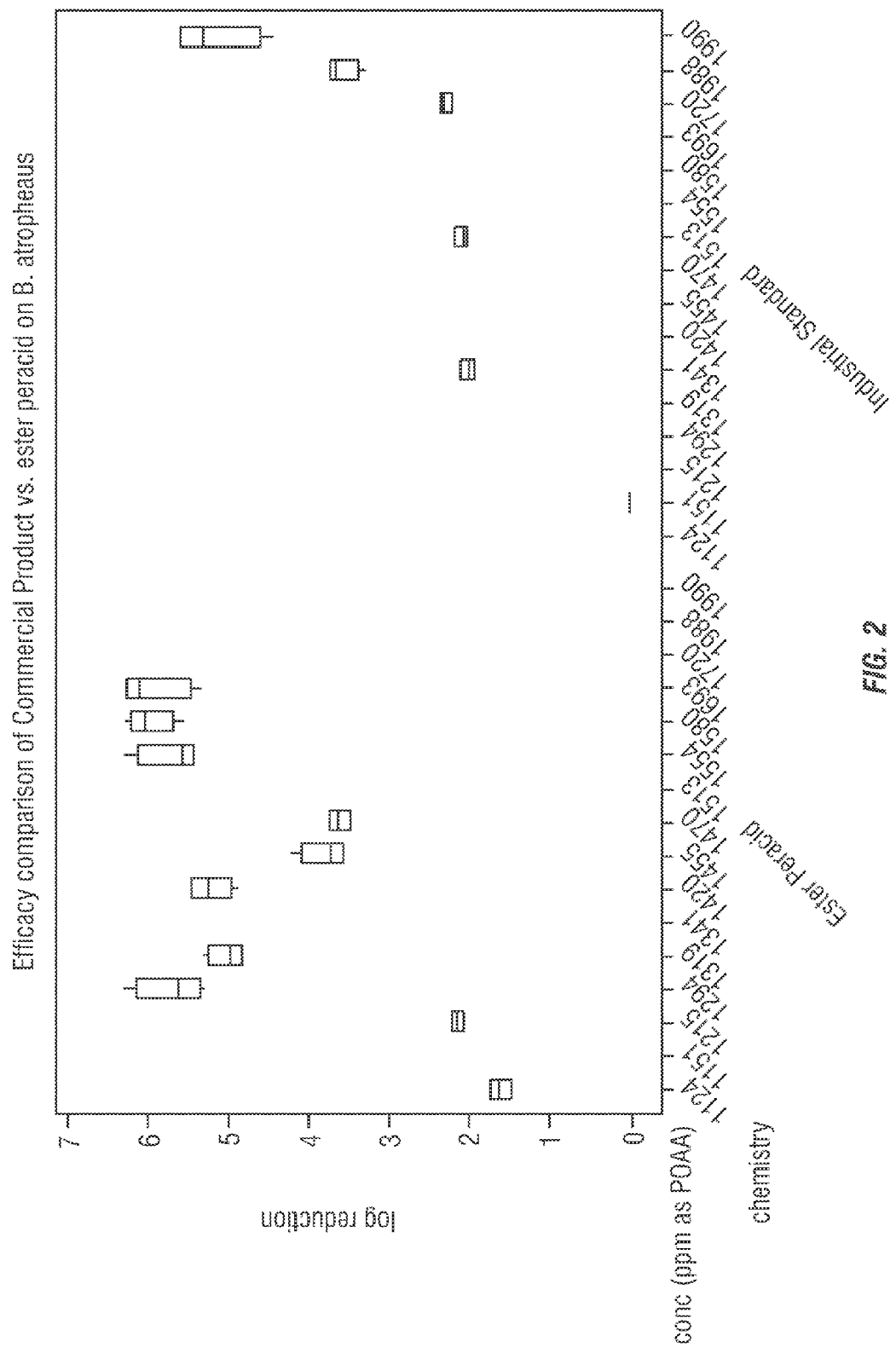

The concentrations required for a 5 log kill of the *Bacillus atropheaus* at the lower use temperature of 50° C. using the same contact time were evaluated for the peracid composition according to embodiments of the invention and the control. As shown in FIG. 2, the concentration of the mixed ester peracid composition of the present invention (Composition C) could be significantly reduced from the industry standard, as well as lowering the delivery temp by 10° C., providing additional benefits for the sterilizing methods.

The inventions being thus described, it will be obvious that the same may be varied in many ways. Such variations are not to be regarded as a departure from the spirit and scope of the inventions and all such modifications are intended to be included within the scope of the following claims.

What is claimed is:

1. A enhanced peroxycarboxylic acid composition for use at reduced concentrations and temperatures comprising:
   at least one $C_1$-$C_{22}$ carboxylic acid;
   at least one $C_1$-$C_{22}$ percarboxylic acid;
   hydrogen peroxide;
   an anionic surfactant comprising a sulfonated percarboxylic acid; and
   an ester species comprising from 0.01 wt-% to 20 wt-%;
   wherein the concentration of the peroxycarboxylic acids is less than 2000 ppm and is effective against *Bacillus* species at temperatures at or below 50° C.

2. The composition of claim 1, wherein the ester species is an alkyl ester.

3. The composition of claim 1, wherein the percarboxylic acids are selected from the group consisting of an alkyl peroxycarboxylic acid, an $C_2$-$C_4$ peroxycarboxylic acids, $C_8$-$C_{12}$ peroxycarboxylic acids, ester peroxycarboxylic acids, alkyl ester peroxycarboxylic acids and combinations of the same, and wherein the sulfonated percarboxylic acid is a persulfonated oleic acid.

4. The composition of claim 1, wherein the composition comprises about 0.01 wt% to 50 wt-% peroxycarboxylic acid about 0.1 wt-% to about 40 wt-% carboxylic acids, and about 0.1 wt-% to about 80 wt-% hydrogen peroxide.

5. The composition of claim 1, wherein the composition does not result in detection of malodors associated with the peroxycarboxylic acid compositions.

6. The composition of claim 1, wherein the composition is stable for at least 1 year at room temperature without the development of malodors.

7. The composition of claim 1, wherein the composition further comprises a surfactant and/or stabilizing agent.

8. The composition of claim 1, wherein the composition is cold stable.

9. An enhanced peroxycarboxylic acid composition for use at reduced concentrations and temperatures comprising:
   at least one C1-C22 carboxylic acid selected from the group consisting of acetic acid, octanoic acid, sulfonated oleic acid and combinations thereof;
   at least one C1-C22 percarboxylic acid selected from the group consisting of peracetic acid, peroctanoic acid, persulfonated oleic acid and combinations thereof;
   hydrogen peroxide;
   an anionic surfactant comprising a sulfonated percarboxylic acid;
   an ester species comprising from 0.01 wt-% to 20 wt-% of the composition; and
   wherein the composition is slightly water insoluble at a use solution, wherein the composition provides a concentration less than 2000 ppm of said C1-C22 percarboxylic acid, wherein the composition is effective against *Bacillus* species at temperatures at or below 50° C., and wherein the ester species provide a pleasant odor masking and/or derivatizing the malodors associated with the percarboxylic acids and carboxylic acids.

10. The composition of claim 8, wherein the ester species is an alkyl ester.

11. The composition of claim 10, wherein the composition does not include a hydrotrope surfactant.

12. The composition of claim 9, further comprising an alcohol selected from the group consisting of methanol, ethanol, propanol, butanol, nonanol, benzyl alcohol and combinations of the same.

13. The composition of claim 12, wherein the alcohol is ethanol and wherein the percarboxylic acid concentration is less than 1750 ppm.

14. A method of reducing population of microorganism on an object at reduced temperatures and concentrations, comprising:
   providing the mixed percarboxylic acid composition of claim 1; and
   contacting an object with the mixed percarboxylic acid composition at a temperature at or below 50° C. without detecting malodors associated with the mixed percarboxylic acid composition.

15. The method of claim 14, wherein the object comprises a food processing or manufacturing surface, food tissue, food packaging, a health care surface, medical or surgical devices, textiles, a body or stream of water, a body or stream of gas, a hospitality sector surface, an industrial sector surface, an agricultural surface, a veterinary surface, architectural surfaces, dishware, hard surface packaging, or a combination thereof.

16. The method of claim 14, wherein the mixed percarboxylic acid composition provides superior reduction in microorganisms and has reduced vapor pressure in comparison to a single percarboxylic acid composition having concentrations of actives above at least 2000 ppm and at temperatures above 60° C.

17. The method of claim 14, wherein the esters are alkyl esters capable of removing and/or masking short chain malodors associated with percarboxylic acid compositions.

18. The method of claim 14, wherein the percarboxylic acid composition is present in an amount effective for reducing a population of a microorganism by at least a 5-log order reduction, wherein the microorganism is selected from the group consisting of spores, bacteria, mold, yeast, viruses and mixtures thereof, and wherein the microorganism is selected from the group consisting of *B. cereus, B. subtilus, B. atropheaus, C. difficile, C. sporogenes, Staph. aureus*, methicillin-resistant *Staph. aureus, Pseudomonas aeruginosa, E. coli* and mixtures thereof.

19. The method of claim 14, further comprising obtaining at least a 5 log reduction of microorganisms.

* * * * *

UNITED STATES PATENT AND TRADEMARK OFFICE
CERTIFICATE OF CORRECTION

Page 1 of 1

PATENT NO.        : 8,883,848 B2
APPLICATION NO.   : 13/542742
DATED             : November 11, 2014
INVENTOR(S)       : Bolduc et al.

It is certified that error appears in the above-identified patent and that said Letters Patent is hereby corrected as shown below:

In the Claims

Col. 46, Claim 10, Line 14:
DELETE after claim "8"
ADD after claim --9--

Signed and Sealed this
Fifteenth Day of September, 2015

Michelle K. Lee
*Director of the United States Patent and Trademark Office*